US012807964B2

(12) United States Patent
Ball et al.

(10) Patent No.: US 12,807,964 B2
(45) Date of Patent: Nov. 24, 2026

(54) MULTI FUNCTIONAL TOXINS

(71) Applicant: Monsanto Technology LLC, St. Louis, MO (US)

(72) Inventors: Timothy K. Ball, Foristell, MO (US); Artem G. Evdokimov, Orchard Park, NY (US); Larry A. Gilbertson, Chesterfield, MO (US); Victor M. Guzov, Cambridge, MA (US); Jeffrey A. Haas, Chesterfield, MO (US); Qing Huai, Winchester, MA (US); Sergey Ivashuta, Ballwin, MO (US); Melissa M. Kemp, Medford, MA (US); Yifei Kong, Chesterfield, MO (US); Thomas M. Malvar, North Stonington, CT (US); Byron V. Olsen, Ballwin, MO (US); Parthasarathy Ramaseshadri, St. Louis, MO (US); Brian E. Weiner, Chapel Hill, NC (US)

(73) Assignee: Monsanto Technology LLC, St. Louis, MO (US)

( * ) Notice: Subject to any disclaimer, the term of this patent is extended or adjusted under 35 U.S.C. 154(b) by 342 days.

(21) Appl. No.: 18/497,825

(22) Filed: Oct. 30, 2023

(65) Prior Publication Data

US 2024/0117374 A1 Apr. 11, 2024

Related U.S. Application Data

(62) Division of application No. 15/217,695, filed on Jul. 22, 2016, now Pat. No. 11,840,700.

(60) Provisional application No. 62/328,543, filed on Apr. 27, 2016, provisional application No. 62/196,249, filed on Jul. 23, 2015.

(51) Int. Cl.

| | |
|---|---|
| ***C12N 15/82*** | (2006.01) |
| ***A01N 37/44*** | (2006.01) |
| ***A01N 37/46*** | (2006.01) |
| ***C07K 14/325*** | (2006.01) |

(52) U.S. Cl.

CPC ......... *C12N 15/8286* (2013.01); *A01N 37/44* (2013.01); *A01N 37/46* (2013.01); *C07K 14/325* (2013.01); *Y02A 40/146* (2018.01)

(58) Field of Classification Search

None

See application file for complete search history.

(56) References Cited

U.S. PATENT DOCUMENTS

| | | | | |
|---|---|---|---|---|
| 7,179,965 | B2 * | 2/2007 | Song .................... | C07K 14/325 800/298 |
| 8,034,997 | B2 | 10/2011 | Bogdanova et al. | |
| 8,269,069 | B1 | 9/2012 | Narva et al. | |
| 8,735,560 | B1 | 5/2014 | English et al. | |
| 9,090,906 | B2 | 7/2015 | Soberón-Chavez et al. | |
| 9,512,187 | B2 | 12/2016 | Je et al. | |
| 9,556,453 | B2 | 1/2017 | Meade et al. | |
| 9,796,983 | B2 | 10/2017 | Narva et al. | |
| 2010/0186123 | A1 | 7/2010 | Pardo-Lopez et al. | |
| 2010/0221238 | A1 | 9/2010 | Flexner et al. | |
| 2014/0073582 | A1 | 3/2014 | Olmos Soto et al. | |

FOREIGN PATENT DOCUMENTS

| | | |
|---|---|---|
| WO | 2016/061392 | 4/2016 |

OTHER PUBLICATIONS

Ho et al (2006, Crop Science 46:781-789).*
Wu et al (2000, FEBS Lett. 473:227-232).*
Baxter et al (2011, Genetics 189:675-679).*
U.S. Appl. No. 15/217,839, filed Jul. 22, 2016, Liu et al.
Badran et al., "Continuous evolution of Bacillus thuringiensis toxins overcomes insect resistance," Nature, 533:58-63, 2016.
Baum et al., "Cotton plants expressing a hemipteran-active Bacillus thuringiensis crystal protein impact the development and survival of Lygus hesperus (Hemiptera: Miridae) nymphs," J Econ Entomol, 105:616-624, 2012.
Esvelt et al., "A system for the continuous directed evolution of biomolecules," Nature, 472:499-503, 2011.
Vaughn et al., "The establishment of two cell lines from the insect Spodoptera frugiperda (Lepidoptera; Noctuidae)" In Vitro, 13:213-217, 1977.
International Search Report for PC/US2016/043691 dated Oct. 21, 2016.
Ho et al. (Crop Science vol. 46 Mar.-Apr. 2006). (Year: 2006).
Liu et al. (Protein Engineering, Design and Selection, vol. 19, Issue 3, Mar. 1, 2006, pp. 107-111). (Year: 2006).
Tounsi et al. (J. Appl. Microbiol. 95:23-28; 2003) (Year: 2003).
De Maagd et al. (Appl. Environ. Microbiol. 65:4369-4374, 1999) (Year: 1999).
Aronson et al. (FEMS Microbiol. Lett. 2001, 195:1-8) (Year: 2001).
Bohorova et al. (Theor. Appl. Genet. (2001) 103:817-826) (Year: 2001).

(Continued)

*Primary Examiner* — Anne Kubelik

(74) *Attorney, Agent, or Firm* — Dentons US LLP; David Lanzotti

(57) ABSTRACT

Pesticidal proteins are provided that combine two or more modes of action into a single molecule. These pesticidal proteins therefor exhibit greater efficacy and/or durability of resistance, for the purposes of pest control, and can be utilized for pest control by provision in the diet of a pest organism, or by topical application to crop plants and/or pests. Methods and compositions for producing and using such proteins are also provided.

12 Claims, No Drawings

Specification includes a Sequence Listing.

(56) References Cited

OTHER PUBLICATIONS

Extended European Search Report regarding Europe Application No. 16828648, mailed Jan. 1, 2019.
Flannagan et al., "Identification, cloning and expression of a CrylAb cadherin receptor from European corn borer, Ostrinia nubilalis (Hubner) (Lepidoptera:Crambidae)", Insect Biochemistry and Molecular Biology, 35(1):33-40, 2005.
Fujii et al., "Cry1Aa binding to the cadherin receptor does not require conserved amino acid sequences in the domain II loops", Bioscience Reports, 33(1):103-112, 2013.
Likitvivatanavong et al., "Multiple Receptors as Targets of Cry Toxins in Mosquitoes", Journal of Agriculture and Food Chemistry, 59(7):2829-2838, 2011.
Pardo-Lopez et al., "Bacillus thuringiensis insecticidal three-domain Cry toxins: mode of action, insect resistance and consequences for crop protection", 37(1):3-22, 2013.
Tanaka et al., "The ATP-binding cassette transporter subfamily C member 2 in Bombyx mori larvae is a functional receptor for Cry toxins from Bacillus thuringiensis", FEBS Journal, 280(8):1782-1794, 2013.
Kim, Yang-Su, et al. "Mutagenesis of Bacillus thuringiensis cry1Ac gene and its insecticidal activity against Plutella xylostella and Ostrinia furnacalis." Biological Control 47.2 (2008): 222-227. (Year: 2008).
Shan, Shiping, et al. "A Cry1Ac toxin variant generated by directed evolution has enhanced toxicity against Lepidopteran insects." Current microbiology 62.2 (2011): 358-365. (Year: 2011).
Packer, Michael S., and David R. Liu. "Methods for the directed evolution of proteins." Nature Reviews Genetics 16.7 (2015): 379-394. (Year: 2015).
GenBank Accession AAU87037.1, available online on Feb. 25, 2005 (Year: 2005).
Flagel et al., 2018, Sci Rep 8, 7255. https://doi.org/10.1038/s41598-018-25491-9.
Heckel, 2020, Arch. Insect. Biochem. Physiol. 104:e21673, https://doi.org/10.1002/arch.21673.
Wang et al, 2018, Reg. Toxicol. Pharmacol. 99: 50-60.

* cited by examiner

MULTI FUNCTIONAL TOXINS

REFERENCE TO RELATED APPLICATION

This application is a divisional of U.S. patent application Ser. No. 15/217,695, filed Jul. 22, 2016, which claims the benefit of U.S. Provisional Application No. 62/196,249, filed Jul. 23, 2015, and U.S. Provisional Application No. 62/328,543, filed Apr. 27, 2016, each of which is herein incorporated by reference in its entirety.

INCORPORATION OF SEQUENCE LISTING

The sequence listing that is contained in the file named MONS395USD1 ST26.xml", which is 26,714 bytes in size (measured in MS-Windows) and was created on Oct. 26, 2023, is filed herewith by electronic submission and is incorporated herein by reference.

FIELD OF THE INVENTION

The invention generally relates to the field of insect inhibitory proteins. Novel insect inhibitory or pesticidal proteins with altered binding to one or more insect receptor(s), and that exhibit insect inhibitory activity against pests of crop plants, are disclosed. In particular, the disclosed proteins are insecticidally active against agriculturally-relevant pests of crop plants and seeds, particularly Coleopteran, Lepidopteran. and Hemipteran species of insect pests. Plants, plant parts, and seeds containing a recombinant polynucleotide construct encoding one or more of the disclosed toxin proteins are also provided.

BACKGROUND OF THE INVENTION

Many insect-pesticidal proteins exert their pesticidal effects by flirt binding to a target receptor on or near the surface of a cell within the target insect pest, and then forming a pore in the membrane to which the target pest receptor is on, or is embedded within. Thus, if a target pest becomes resistant to the pesticidal protein, the underlying cause of the resistance that the pest has developed may be a result of a change in the interaction between the pesticidal protein and the target receptor of the insect cell. The binding of a pesticidal protein to a cognate receptor in a target pest, allowing the pesticidal protein to exert its pesticidal effects upon that pest, is considered to be a "mode of action" (MOA). The inability of a pesticidal protein to bind to its cognate receptor may be referred to as a "loss of the mode of action" of that pesticidal protein. The loss of a mode of action typically results in the target pest becoming resistant to that particular pesticidal protein. Such pesticidal proteins am not typically known to exhibit the ability to bind to more than one receptor in the target pest.

An important goal in the field of Agricultural Biotechnology as it relates to insect pest control is to avoid or delay the development of resistance to an inhibitory or insecticidal protein in a population of insect pests targeted by a particular pesticidal protein. Providing two or more modes of action in the diet of a target pest can delay or reduce the chance that an insect pest may develop such resistance. Two or more modes of action may be provided as at least two different pesticidal proteins that am both toxic to the same insect species but which each bind to different receptors. This approach has been referred to as the dual mode of action approach. Future products considered by the agriculture industry include developing crop plants with at least two modes of action, provided by two or mom different pesticidal proteins each toxic to the same insect species but each providing the pesticidal effect as a result of binding to different receptors.

Thus there is a need in the art to be able to provide as many modes of action for controlling any single crop pest as possible in a single plant genome in order to reduce the likelihood of target pests developing resistance to a single mode of action. The prior art has not taught that multiple modes of action could be provided by a single protein toxin or by a single pesticidal protein which has been engineered to have the ability to bind to different receptors within the same target pest and confer effective pesticide activity upon the target pest.

SUMMARY OF THE INVENTION

In one aspect, the invention provides a method for controlling an infestation by a target pest in a crop, said method comprising: contacting said target pest with a pesticidal protein that binds to a rust receptor and a second receptor of the target pest; wherein the first receptor is different from the second receptor; and wherein the binding to the second receptor does not interfere with the binding to the rust receptor. In one embodiment of the method, the pesticidal protein is provided within the diet of the target pest. In another embodiment of the method, the pesticidal protein is topically applied to the crop or the target pest. In some embodiments the pesticidal protein does not naturally bind to both the rust receptor and the second receptor.

In certain embodiments the pesticidal protein is engineered to enable or improve binding to the first receptor or the second receptor. In some embodiments the pesticidal protein is engineered by a method for protein modification selected from the group consisting of: rational design, structure based design, semi-rational design, directed evolution, phage display, selection of peptides from a peptide library for inclusion in the pesticidal protein for targeting the pesticidal protein to bind to a receptor, operable linkage of the pesticidal protein to an antibody, antibody binding domain, alphabody, lipocalin, anticalin, random mutagenesis, rational design, structure based design, semi-rational design, high throughput optimization focusing on the study of 3D protein toxin models and selecting surface exposed features into which changes can be introduced, and construction of chimeric proteins produced from segments of two or more different proteins.

The invention further provides a method wherein the pesticidal protein is expressed in a plant of the crop in which pest infestation is controlled. Thus, in certain embodiments the pesticidal protein is encoded by a polynucleotide molecule incorporated in the genome of the plant.

Also provided by the invention are embodiments wherein the first receptor or the second receptor is a pest cell surface protein or an insect protein. Contemplated methods may further comprise providing to the target pest a pesticidal agent that is different from the pesticidal protein and is selected from the group consisting of a bacterial toxin, a plant toxin, an arachnid toxin, a venom toxin, and a dsRNA targeting for suppression of an essential gene in said target pest. In certain embodiments the pesticidal agent is selected from the group consisting of Cry1A, Cry1Aa, Cry1Ab, Cry1Ac, Cry1A.105, Cry1B, Cry1Bb1, Cry1C, Cry1Ca, Cry1C amino acid sequence variants, Cry1D, Cry1Da, Cry1D amino acid sequence variants, Cry1E, Cry1F, Cry1Fa. Cry1G, Cry1H, Cry1I, Cry1J, Cry1K, Cry1L, Cry2A, Cry2Aa, Cry2Ab, Cry2Ae, Cry3, Cry3Aa, Cry3A amino acid sequence variants, Cry3B, Cry3Bb. Cry3Bb amino acid sequence variants, Cry4B, Cry5, Cry6, Cry7, Cry8, Cry9, Cry15, Cry34, Cry35, Cry43A, Cry43B, Cry51Aa1, ET29, ET33, ET34, ET35, ET66, ET70, Cry1A.105, TIC400. TIC407, TIC417, TIC431. TIC800, TIC807. TIC834, TIC853, TIC901, TIC1201, TIC1415, TIC3131, VIP3A, VIP3B, 5307, Axmi184, Axmi205, eHIP toxin proteins, insecticidal DIG proteins, venom proteins, and the insecticidal core toxin of each of the foregoing. In some embodiments, a) the pesticidal agent is toxic to the same pest as the pesticidal protein; or b) the pesticidal agent is toxic to a different pest than the pesticidal protein.

In particular embodiments the pesticidal agent is a protein that binds to a third receptor. In some embodiments, the pesticidal agent is engineered to bind to a fourth receptor, and wherein said third receptor and said fourth receptor are different, and binding of said pesticidal agent to said fourth receptor does not interfere with binding to said third receptor.

In certain embodiments the target pest is selected from the group consisting of a Lepidopteran insect, a Coleopteran insect, a Hemipteran insect, a Homopteran insect, a Hymenopteran insect, a Dipteran insect, a nematode, a pathogenic microorganism, a pathogenic fungi, and a pathogenic bacterium. The invention further provides embodiments wherein the crop comprises a monocotyledonous plant or a dicotyledonous plant. In certain embodiments the monocotyledonous plant is selected from the group consisting of rice, wheat, barley, grasses, bentgrass, sugarcane, oats, sorghum, chives, shallots, and corn; or the dicotyledonous plant is selected from the group consisting of cotton, canola, soybean, beans, sugarbeet, alfalfa, vegetables, fruits, cucurbits, melons, pigeonpea, peppers, and peanut.

Another aspect of the invention relates to a pesticidal protein that binds to at least a first receptor and a second receptor of a target pest; wherein the first receptor is different from the second receptor, wherein the binding to the second receptor does not interfere with the binding to the first receptor, and wherein the pesticidal protein does not naturally bind to both the first receptor and the second receptor. In some embodiments, the pesticidal protein comprises or displays enhanced pesticidal activity as compared to a pesticidal protein that binds to only one of the first receptor or the second receptor. In certain embodiments the pesticidal protein is encoded by a polynucleotide molecule incorporated in the genome of a plant. In particular embodiments the pesticidal protein is selected from the group consisting of: an insecticidal toxin, a nematicidal protein, a fungicidal protein, or a bacteriocidal protein. Thus in some embodiments the insecticidal toxin is selected from the group consisting of: a Bt toxin, a *Bacillus* species insecticidal toxin other than a Bt toxin, a Photorhabdus insecticidal toxin, a Xenorhabdus insecticidal toxin, a chimeric toxin, an arachnid insecticidal toxin, and a lectin. In particular embodiments the chimeric toxin comprises a toxin fusion with a partner protein or a toxin protein produced from the fusion of two or more portions of different Bt toxins.

In certain embodiments the target pest is selected from the group consisting of a Lepidopteran insect, a Coleopteran insect, a Hemipteran insect, a Homopteran insect, a Hymenopteran insect, a Dipteran insect, a nematode, a pathogenic microorganism, a pathogenic fungi, and a pathogenic bacterium.

Yet another aspect of the invention relates to a plant or plant cell comprising a pesticidally effective amount of the pesticidal protein that binds to at least a rust receptor and a second receptor of a target pest; wherein the first receptor is different from the second receptor; wherein the binding to the second receptor does not interfere with the binding to the first receptor, and wherein the pesticidal protein does not naturally bind to both the first receptor and the second receptor. A seed produced from such a plant, wherein the seed comprises a polynucleotide molecule encoding the pesticidal protein in its genome, is also contemplated.

In certain embodiments, the plant or plant cell further comprises: a) a pesticidal agent toxic to the target pest, wherein the pesticidal agent is different from the pesticidal protein and is selected from the group consisting of a bacterial toxin, a plant toxin, an arachnid toxin, and a dsRNA targeting for suppression an essential gene in said target pest; or b) a pesticidal agent toxic to a different pest, wherein said pesticidal agent is different from said pesticidal protein and is selected from the group consisting of a bacterial toxin, a plant toxin, an arachnid toxin, and a dsRNA targeting for suppression an essential gene in said different pest.

Another aspect of the invention provides a recombinant polynucleotide molecule encoding the pesticidal protein that binds to at least a first receptor and a second receptor of a target pest; wherein the first receptor is different from the second receptor; wherein the binding to the second receptor does not interfere with the binding to the first receptor, and wherein the pesticidal protein does not naturally bind to both the first receptor and the second receptor. A polynucleotide construct comprising the recombinant polynucleotide molecule is also provided.

Further contemplated is a composition comprising the pesticidal protein, formulated for topical application to the target pest or to a crop plant.

Another aspect of the invention provides a method for controlling crop pest infestation by a first target pest and a second target pest different from the first, comprising: providing in the diet of the rust and the second target pests a pesticidal protein that binds to a first receptor in the gut of the first target pest and to a second receptor in the gut of the second target pest, wherein said first receptor and second receptor are not the same. In one embodiment of such a method, the pesticidal protein is engineered to enable or improve binding to the first receptor or the second receptor, and wherein the pesticidal protein does not naturally bind to both the first receptor and the second receptor.

Also provided is a method for reducing the number of pesticidal proteins or polynucleotide molecules encoding a pesticidal protein to be included in a crop species for controlling a first target pest and a second target pest different from the first, comprising: providing in the genome of the crop species a polynucleotide molecule encoding a pesticidal protein that binds a first receptor in the first target pest and a second receptor in the second target pest, wherein said first receptor is different from said second receptor.

Thus, in another aspect, there is provided a crop grown in a field, wherein the crop comprises a polynucleotide molecule encoding a pesticidal protein that controls a) a single target pest of said crop, wherein said pesticidal protein is engineered to contain two or more modes of action for controlling said single target pest; or b) a first target pest of said crop by binding to at least one first receptor in said first target pest, and a second target pest of said crop by binding to at least one second receptor in said second target pest, wherein said second receptor is different than the first receptor and said second target pest is different from said first target pest.

BRIEF DESCRIPTION OF THE SEQUENCES

SEQ ID NO:1 is the amino acid sequence of full-length Cry1Ac1 toxin.

SEQ ID NO:2 is the amino acid sequence of PACE-derived Cry1Ac1 toxin variant Protein 3.

SEQ ID NO:3 is the amino acid sequence of PACE-derived Cry1Ac1 toxin variant Protein 4.

SEQ ID NO:4 is the amino acid sequence of PACE-derived Cry1Ac1 toxin variant Protein 5.

SEQ ID NO:5 is the amino acid sequence of TIC2160 toxin.

SEQ ID NO:6 is the amino acid sequence of a *Spadoptera frugiperda* (fall armyworm) cadherin binding peptide: VDWWSPFYDRLK.

SEQ ID NO:7 is the amino acid sequence of TIC2160* toxin variant, comprising the Sf cadherin binding protein of SEQ ID NO:6 inserted into Domain 4 of TIC2160 (SEQ ID NO:5).

SEQ ID NO:8 is the amino acid sequence of full-length TIC105 toxin.

SEQ ID NO:9 is the amino acid sequence of a *Spadoptera frugiperda* (fall armyworm) cadherin binding peptide: SDYGWWRPFQPG.

SEQ ID NO:10 is the amino acid sequence of a TIC105 toxin variant, comprising the Sf cadherin binding protein of SEQ ID NO:9 inserted into the TIC105 scaffold (SEQ ID NO:8).

SEQ ID NO:11 is the amino acid sequence of a Cry1Ac1 toxin variant, comprising the Sf cadherin binding protein of SEQ ID NO:6 inserted into the Cry1Ac1 scaffold (SEQ ID NO:1).

SEQ ID NO:12 is the amino acid sequence of PACE-derived TIC105 toxin variant IS0349 comprising the following mutations to TIC105 (SEQ ID NO:8): F328Y. S404I, E461G. N463C, A467R, S468G. H480Y, T481A, Q483H. Y510C, R524C, D556N, S580R, T608A. E612Q, N616D.

SEQ ID NO:13 is the amino acid sequence of chimeric cadherin derived from *Spodoptera frugiperda* (fall army-worm) cadherin and *Chrysodeixis includens* (soybean looper) cadherin.

DETAILED DESCRIPTION OF THE INVENTION

The present invention provides novel methods for producing multifunctional insect-active pesticidal proteins displaying one or more additional mode(s) of action relative to an unmodified or wild-type pesticidal protein which does not comprise such modification. Such multifunctional proteins am also provided by the invention. In particular, the present methods allow for identification, for instance via directed evolution or any other method known for producing variant polypeptide sequences, of polypeptide sequences which allow for functional interaction (e.g. binding) to a "receptor" protein present in an insect cell. A protein comprising the identified polypeptide sequence responsible for the newly identified binding may then be utilized for enhanced insect control, or for instance, the identified polypeptide sequence conferring novel binding activity may be added to a pre-existing protein, such as an insecticidal toxin which in its native form does not interact with a receptor present in a given insect cell, or on the surface of such insect cell including an insect gut cell, to create a modified protein exhibiting an additional mode of action ("MOA") for insect pest control.

Such addition of polypeptide sequence to result in a broader spectrum of interaction with insect receptor(s) can surprisingly be performed without affecting the functional activity of the modified protein regarding the original receptor with which the corresponding wild-type protein typically interacts. Thus the present invention allows for producing a modified pest control protein with an enhanced spectrum of activity against one or more additional insect pests, relative to the spectrum of activity typically seen for the corresponding (i.e. "scaffold") wild-type pesticidal protein. Such a modified protein may not only exhibit a novel spectrum of insecticidal activity, but may also be useful for delaying, or reducing the likelihood of, development of resistance to a given insect control protein in an insect population.

Pesticidal proteins that are delivered in the diet of a pest generally exert their pesticidal effects by first binding to a target pest receptor on or near the surface of a cell within the target pest, resulting in formation of a pore in the membrane to which the target pest receptor is on, or is embedded within. Pore formation causes cell membrane damage; the pest typically ceases eating, becomes dehydrated, and/or stunted and subsequently dies. The step of binding is critical and, for any particular pest being targeted for control by the pesticidal protein, binding occurs to only one particular receptor which is generally a protein that is produced by the target pest and is surface exposed, I.e., exposed on the surface of the gut membrane that is exposed to the biological materials consumed as food by the pest and which pass through the insect alimentary canal, the gut of the pest.

It is generally recognized that such pesticidal proteins are not known to exhibit the ability to bind to more than one receptor in the target pest. Thus in the event that the target pest evolves to become resistant to a pesticidal protein, the underlying cause of the resistance that the pest has developed may be a result of loss of expression of the target receptor to which the pesticidal protein binds; alternatively some feature of the target receptor may have changed, resulting in the loss of recognition for binding by the previously active pesticidal protein. It is also generally recognized that the first receptor to which a pesticidal protein binds in a first target pest and exerting some biological effect upon such first target pest analogous to controlling the first target pest, is also a receptor that exhibits a binding epitope that is substantially similar if not the same as a binding epitope on a second receptor in a second target pest that is also capable of being controlled by the same pesticidal protein. For example, a toxin protein that controls a corn earworm and also controls a pink bollworm is generally recognized as targeting for binding the same or a similar epitope.

By reference to control, controlling, or controlled, with reference to pest control, insect control, nematode control, and the like, it is intended to mean the feature of stunting, mortality, cessation of feeding, repulsion, or absence of damage to a particular crop or plant tissue (such as flower, stem, leaf, seed, fruit, and root) and the like, a property that can be observed by those of ordinary skill in the art.

The binding of a pesticidal protein to a single receptor in a target pest so that the pesticidal protein can exert its pesticidal effects upon that pest is considered to be a mode of action (MOA). Loss of the pesticidal proteins' ability to exert its pesticidal effects upon the target pest because of the inability of the pesticidal protein to bind to its cognate receptor is referred to as a loss of the mode of action of that pesticidal protein. The loss of a mode of action results in the target pest becoming resistant to that particular pesticidal protein.

An effective mechanism to avoid the development of resistance of a population of pests targeted by a particular pesticidal protein is to provide in the diet of the target pest two or more modes of action for pest control. Typically in the art, as an approach for providing two or more modes of action, at least two different pesticidal proteins may be provided, that are both toxic to the same insect species but which each bind to different receptors. In controlling insect pests in crop fields, this approach has been referred to as the dual mode of action approach, and when *Bacillus thuringiensis* protein toxins are used to convey these modes of action in transgenic plants expressing such toxin proteins, the plant product may be characterized as a plant conveying "dual Bt's" or "dual modes of action."

It may be advantageous to include in engineered crop plants at least two modes of action by providing two or more different pesticidal proteins each toxic to the same insect species, but each providing their pesticidal effect as a result of binding to a different receptor present in a target insect pest. However, the ability to stack sequences for plant expression, whether in a single vector that is introduced into the transgenic plant, or in multiple vectors that are also introduced into the genome of the plant but in different places in the plant genome, is becoming increasingly difficult, even though mechanisms for site directed integration or gene editing am being developed for use in many of the principle crops in cultivation today. Thus there is a need in the art to be able to provide as many modes of action for controlling any single crop pest as possible on or in a single plant, and within the plant genome, in order to reduce the likelihood of development of resistance of any single target pest to any one of these several (multiple) modes of action. No prior art has taught that the multiple modes of action could be provided by a single pesticidal agent, whether the pesticidal agent is a chemical agent or a protein toxin. No prior art has taught or disclosed the providing of a single pesticidal protein into which the ability to bind to different receptors within the same target pest has been engineered (i.e., incorporated) and to confer effective pesticide activity upon the target pest regardless of the receptor that is bound by the pesticidal protein. No prior art has taught or disclosed that in any such protein, the binding of one receptor by the pesticidal protein does not diminish or reduce the ability of the pesticidal protein to bind to any other receptor, and vice versa.

The present invention thus provides approaches for controlling pests in the field that have previously developed resistance to a particular field exposed toxin. For example, a Cry1Ac resistant cabbage looper that was previously sensitive to Cry1Ac can now be controlled by introducing into a plant a Cry1Ac amino acid sequence variant that exerts its effects upon cabbage looper by binding to an additional or two or more different receptors exposed on the surface of the cells in the gut of cabbage looper larvae. In the event that one of these receptors is not present or is no longer present in a given target insect population, the other receptor can function to allow for Cry1A binding and to introduce a pore into the gut of the looper, causing insect morbidity and mortality, thus controlling the pest.

While the described features of the invention am generally applicable to any protein toxin and the disclosure herein primarily relates to Bt toxins, one of ordinary skill in the art will recognize that these principles are generally applicable across all fields of toxin science. The present invention is generally applicable to any toxin or pesticidal protein including but not limited to Cry1A, Cry1Aa, Cry1Ab, Cry1Ac, Cry1A.105, Cry1B, Cry1Bb1, Cry1C. Cry1Ca, Cry1C amino acid sequence variants, Cry1D, Cry1Da, Cry1D amino acid sequence variants, Cry1E, Cry1F, Cry1Fa, Cry1Fa truncated protein toxins or amino acid sequence variants. Cry1G, Cry1H, Cry1, Cry1J, Cry1K, Cry1L, Cry2A, Cry2Aa, Cry2Ab. Cry2Ae, Cry3. Cry3Aa. Cry3A amino acid sequence variants, Cry3B, Cry3Bb. Cry3Bb amino acid sequence variants. Cry4B. Cry5. Cry6. Cry7, Cry8, Cry9, Cry15. Cry34, Cry35, Cry43A, Cry43B, Cry51Aa1, ET29. ET33, ET34. ET35, ET66, ET70. Cry1A.105. TIC400. TIC407, TIC417. TIC431. TIC800, TIC807. TIC834, TIC853, TIC901, TIC1201, TIC1415, TIC3131. VIP3A, VIP3B, 5307, Axmi184, Axmi205, eHIP toxin proteins, insecticidal DIG proteins, venom proteins, and including the insecticidal core toxin of each of the foregoing.

In some aspects, this disclosure provides variant Br toxins that are derived from a wild-type Bt toxin and have at least one variation in the amino acid sequence of the protein as compared to the amino acid sequence present within a cognate wild-type Bt toxin or at least one variation in the encoding nucleic acid sequence that results in a change in a codon that results in an amino acid change in the amino acid sequence present within a cognate wild type Bt toxin. The variation in amino acid sequence generally results from a mutation, insertion, or deletion in a DNA coding sequence. Mutation of a DNA sequence can result in a nonsense mutation (e.g., a transcription termination codon (TAA, TAG, or TAA, i.e. amber, ocher, and opal mutations) that produces a truncated protein), a missense mutation (e.g., an insertion or deletion mutation that shifts the reading frame of the coding sequence), or a silent mutation (e.g., a change in the coding sequence that results in a codon that codes for the same amino acid normally present in the cognate protein, i.e., a synonymous mutation, or introduces an amino acid substitution which does not alter the cognate proteins' functionality). In some embodiments, mutation of a DNA sequence results in a non-synonymous (i.e., conservative, semi-conservative, or radical) amino acid substitution.

It has been discovered as described herein that pesticidal proteins can be amended, modified, or altered to exhibit two or mom modes of action as a result of causing the pesticidal protein to bind to more than one receptor in any particular target pest intended for control by using the pesticidal protein.

By reference to amended, modified or altered, it is intended that a particular amino acid sequence of a particular pesticidal protein be changed in any number of ways known in the art to achieve the properties intended as set forth in this application. For example, a protein's amino acid sequence can be amended, modified, or altered by engineering into such protein amino acid sequence certain changes that are result effective in achieving the properties described herein. The skilled artisan can insert additional (i.e., supplemental) amino acids to add to the native amino acid sequence, for example by introducing peptides of various lengths (from two or more consecutive amino acids up to several dozen consecutive amino acids, but more preferably from about five consecutive amino acids to any length of amino acids from five to about fifty consecutive amino acids, i.e., a peptide of such length of amino acids).

Surprisingly, it is found that an additional epitope may be introduced into a pesticidal protein such as a Bt protein, that allows for its binding to a receptor that is different from the normal cognate receptor to which the pesticidal protein binds in the ordinary course, and without significantly changing the normal receptor binding epitope nor changing the toxic properties typically conferred by such pesticidal protein when it binds to the normal receptor in a particular target pest. Changes to a pesticidal protein may also include deletion of consecutive amino acids to introduce new binding epitopes without modifying the ordinary normal cognate receptor binding epitope, and changing various amino acids within the amino acid sequence of the pesticidal protein in order to cause the pesticidal protein to bind supplemental epitopes/receptors without changing the pesticidal proteins' normal cognate receptor binding capability and without changing the pesticidal proteins' normal pesticidal capabilities. In addition, reference to amended, modified and altered and methods for introducing such changes into a proteins' amino acid sequence can include de now engineering of a nucleotide sequence to reflect the changed amino acid sequence, constructing a novel amino acid sequence to encode such altered, amended or modified amino acid sequence, or evolving a nucleotide sequence to reflect the changes to be introduced into such pesticidal protein amino acid sequence. All such methods for introducing such changes result in varying the amino acid sequence to introduce supplemental amino acids, whether single changes at specific amino acid positions normally within the naturally occurring amino acid sequence (i.e., substitutions of one amino acid for another, whether conserved changes or non-conserved changes) or introducing or deleting/removing consecutive amino acids (peptides) within the pesticidal protein amino acid sequence.

Wild-type Bt toxins are encoded by genes of the cry gene family, e.g., by the Cry1Ac gene. The amount or level of variation between a wild-type Bt toxin and a variant Bt toxin provided herein can be expressed as the percent identity of the nucleic acid sequences or amino acid sequences between the two genes or proteins. In some embodiments, the amount of variation is expressed as the percent identity at the amino acid sequence level.

The amount or level of variation between a wild-type Bt toxin and a variant Bt toxin can also be expressed as the number of mutations present in the amino acid sequence encoding the variant Bt toxin relative to the amino acid sequence encoding the wild-type Bt toxin. In some embodiments, an amino acid sequence encoding a variant Bt toxin comprises between about 1 mutation and about 100 mutations, about 10 mutations and about 90 mutations, about 20 mutations and about 80 mutations, about 30 mutations and about 70 mutations, or about 40 and about 60 mutations relative to an amino acid sequence encoding a wild-type Bt toxin. In some embodiments, an amino acid sequence encoding a variant Bt toxin comprises more than 100 mutations relative to an amino acid sequence encoding a wild-type Bt toxin.

The location of mutations in an amino acid sequence encoding a variant Bt toxin are also contemplated by the disclosure. Generally, mutations may occur in any portion (e.g., N-terminal, interior, or C-terminal) of an amino acid sequence. Mutations may also occur in any functional domain (e.g., the pore-forming domain, the receptor-binding domain, or the sugar-binding domain). In some embodiments, at least one mutation is located in the receptor-binding domain of the Bt variant toxin (i.e., that portion of the Bt variant toxin that interacts with the TBR).

In some aspects, the disclosure relates to variant Bt toxins that bind to receptors in Bt toxin-resistant pests with higher affinity than the wild-type Bi toxin from which they are derived (e.g., Cry1Ac, represented by SEQ ID NO: 1). Generally, binding of a Bt toxin to a receptor is mediated by the interaction between the receptor binding domain (e.g., target binding region) of the Bt toxin and the cell surface receptor of the target cell. Thus, in some embodiments the disclosure provides a protein comprising a receptor binding domain, wherein the receptor binding domain comprises an amino acid sequence that is at least 70%, at least 75%, at least 80%, at least 85%, at least 90%, at least 95%, or at least 99% identical to SEQ ID NO: 1, wherein the receptor binding domain comprises at least one mutation.

This disclosure relates, in part, to the discovery that pesticidal proteins can be engineered to bind more than one receptor, particularly to bind a receptor that the pesticidal protein would not ordinarily bind to in nature. Such methods include but are not limited to protein modification methods such as rational design, structure based design, semi-rational design, directed evolution (including but not limited to shuffling methods for evolving coding sequences to produce modified or variant amino acid sequences, phage assisted evolution for evolving coding sequences to produce modified or variant amino acid sequences, and the like), phage display methods for selecting modified peptides capable of binding particular target moiety/epitope, selection of peptides from a peptide library that are capable of binding a particular target moiety/epitope for inclusion in the pesticidal protein for targeting the pesticidal protein to bind to a receptor to which the pesticidal protein lacking the peptide would have no binding affinity, operable linkage of the pesticidal protein to an antibody, operable linkage of the pesticidal protein to an antibody binding domain, operable linkage of the pesticidal protein to an alphabody, operable linkage of the pesticidal protein to an lipocalin, operable linkage of the pesticidal protein to an anticalin, random mutagenesis to obtain an amino acid sequence variant capable of binding a second receptor, rational design of denovo amino acid sequences capable of binding to a first receptor and to a second receptor that is different from the first, structure based design of denovo amino acid sequences capable of binding to a first receptor and to a second receptor that is different from the first, semi-rational design of denovo amino acid sequences capable of binding to a first receptor and to a second receptor that is different from the first, for example high through put optimization focusing on the study of 3D protein models of a cognate toxin and selecting surface exposed features into which changes (such as amino acid sequence changes, or inclusion or deletion of peptide segments) can be introduced.

Also, chimeragenesis to achieve the features taught here is included as a method for producing a protein that exhibits more than one mode of action when used in a particular target pest. A chimeric protein may bind to one or more receptors that are different from each other compared to the receptors that to which the underlying non-chimeric toxins from which the chimeric protein was constructed bind. For example, a chimeric toxin produced from a Cry1 Ab and a Cry1Fa may provide for binding to more than one receptor in a particular targeted pest.

Such methods are useful for producing variant Bt toxins (or other pesticidal proteins) that have altered binding capabilities. In some embodiments, a variant Bt toxin binds to a toxin binding region of a cell surface receptor with higher affinity than the cognate Bt toxin. Several cell surface receptors are known in the art. Examples of cell surface receptors include, but are not limited to, cadherin-like proteins (CADR), glycosylphosphatidyl-inositol (GPI)-anchored aminopeptidase-N (APN), and GPI-anchored alkaline phosphatase (ALP), however, Cry1Ac does not bind to, or recognize, each of these as a target receptor. A variant Bt toxin that binds with higher affinity can have an increase in binding strength ranging from about 2-fold to about 100-fold or greater, about 5-fold to about 50-fold, or about 10-fold to about 40-fold, relative to the binding strength of the wild-type Bt toxin from which the variant Bt toxin was derived. Binding strength can be measured or determined using any suitable method known in the art, for example by determining the dissociation constant (Kd) of an interaction. The skilled artisan will generally understand the metes and bounds of these methods.

In some aspects, the disclosure relates to the surprising discovery that toxins that bind to more than two different receptors in a particular target pest are effective in killing pests with greater efficacy and are more durable. In addition, such engineered toxins are capable of restoring the ability to control a pest that has become refractory or resistant to treatment with the wild-type Bt toxin from which the variant Bt toxins are derived.

Variant Bt toxins described by the disclosure may be effective against a wide variety of pests, for example insects. In some embodiments, the insects are selected from the group consisting of the insect Orders Lepidoptera, Coleoptera, Hemiptera, and Diptera, including adults, pupae, larvae and neonates.

Insects of the order Lepidoptera include, but are not limited to, armywonns, cutworms, loopers, and heliothines in the Family Noctuidae, e.g., fall armyworm (*Spadoptera frugiperda*), beet armyworm (*Spodoptera exigua*), bertha armyworm (*Mamestra configurata*), black cutworm (*Agrotis ipsilon*), cabbage looper (*Trichoplusla ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera. e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm). *Archips argyrospila* (fruit tree leaf roller), *Archips rosana* (European leafroller) and other *Archips* species, *Chilo suppressalis* (Asiatic rice borer, or rice stem borer), *Cnaphalocrocis medinalis* (rice leaf roller). *Crambus caliginosellus* (corn root webworm). *Crambus teterrellus* (bluegrass webworm). *Diatraea grandiosella* (southwestern corn borer). *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly). *Pieris rapae* (imported cabbageworm, or small white butterfly). *Plutella xylostella* (diamondback moth). *Spodoptera exigua* (beet armyworm), *Spodoptera litura* (tobacco cutworm, cluster caterpillar), and *Tuta absoluta* (tomato leafminer). Other examples of Lepidoptera include *Zeuzera coffeae, Hyalarcta* spp., *Eumeta* spp., *Manduca sexta, Manduca quinquemaculata, Peridroma saucia, Colias eurytheme, Plathypena scabra, Trichoplusia ni, Evergestos ro, Evergestos psa, Evergestos os* and *Phthorimaea operculella*.

Contemplated insects of the order Coleoptera include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata. Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarbeidae, Sitophilus* spp., *Sitotraga* spp., *Tenebrio* spp., *Tribolium* spp. and *Trogoderma* spp. particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm. MCR). *Diabrotica balteata* (Brazilian Corn Rootworm (BZR), *Diabrotica undecimpunctata howardii* (Southern Corn Rootworm. SCR) and a Brazilian Corn Rootworm complex (BCR) consisting of *Diabrotica viridula* and *Diabrotica speciosa*). Other examples of Coleoptera include *Agroites mancus, Limonius agonu*, white grub, *Chaetocnema pulicaria, Carpophilus lugubris, Popillia japonica, Epitrix cucumeris, Epitrix fuscula, Systena blanda, Cerotoma trifurcate, Epilachna varivestis, Phyllotreta striolata, Phyllotreta cruciferae, Acalymma vittta, Metriona bicolor, Systena blanda, Crioceris asparagi, Crioceris duodecimpunctata, Disonycha xanthomelas, Epitrix* spp., and *Epicauta* spp.

Examples of Diptera include *Delia platura, Zonosemata electa, Delia radicum, Delia antique, Liriomyza sativae, Pegomya hyoscyami, Anopheles* spp., *Aedes* spp., *Culex* spp., *Onchocerca volvulus. Phlebotomus* spp., *Lutzomyia* spp., *Chrysops* spp., *Tabanus* spp., *Glossina* spp., *Musca domestica*, and *Stomoxys* spp.

Further, them are numerous parasitic nematode species, including various cyst nematodes (e.g. *Heterodera* spp. or *Globodera* spp.), root knot nematodes (e.g. *Meloidogyne* spp.), lesion nematodes (e.g. *Pratylenchus* spp.), dagger nematodes (e.g. *Xiphinema* spp.) and stem and bulb nematodes (e.g. *Ditylenchus* spp.), among others. *Tylenchid* nematodes (members of the order *Tylenchida*), including the families Heteroderidae, Meloidogynidae, and Pratylenchidae, are the largest and most economically important group of plant-parasitic nematodes. Other important parasitic nematodes include reniform nematodes (*Rotylenchulus* species) and *Dorylaimid* nematodes (e.g. *Xiphinema* spp.), among others. Thus improved control of nematodes via multifunctional toxins is also contemplated.

Pathogenic microorganisms contemplated for control may belong to any family of organisms such as, but not limited to prokaryotic organisms, cubacterium, archaebacterium, eukaryotic organisms, yeast, fungi, algae, protozoan, and other parasites. Non-limiting examples of pathogenic microorganism are *Plasmodium falciparum* and related malaria-causing protozoan parasites, *Acanthamoeba* and other free-living amoebae, *Aeromonas hydrophile, Anisakis* and related worms, *Acinetobacter baumanii. Ascaris lumbricoides. Bacillus cereus, Brevundimonas diminuta, Campylobacter jejuni, Clostridium botulinum, Clostridium perfringens, Cryptosporidium parvum, Cyclospora cayetanensis, Diphyllobothrium, Entamoeba histolytica*, certain strains of *Escherichia coli, Eustrongylides, Giardia lamblia, Klebsiella pneumoniae, Listeria monocytogenes, Nanophyetus, Plesiomonas shigelloides, Proteus mirabilis. Pseudomonas aeruginosa, Salmonella, Serratia odorifera, Shigella, Staphylococcus aureus, Stenotrophomonas maltophilia. Streptococcus. Trichuris trichiura, Vibrio cholerae, Vibrio parahaemolyticus, Vibrio vulnificus* and other *vibrios, Yersinia enterocolitica, Yersunia pseudotuberculosis* and *Yersinia kristensenii*.

Illustrative prokaryotes, both Gram-negative and Gram-positive, may include Enterobacteriaceae, such as *Erwinia*; Bacillaceae; Rhizobiaceae, such as *Rhizobium*; Spirillaceae, such as photobacterium, *Zymomonas*; Lactobacillaceae; Pseudomonadaceae, such as *Acetobacter*; Azotobacteraceae, Actinomycetales, and Nitrobacteraceae. Also among eukaryotes are fungi, such as Phycomycetes and Ascomycetes, including *Saccharomyces* and *Schizosaccharomyces*; and *Basidiomycetes*, such as *Rhodotorula, Aureobasidium*, and the like.

In some aspects, this disclosure provides pest control methods comprising providing to a pest a variant Bt toxin. Methods of pest control described herein may therefore be useful for controlling pests that are resistant to treatment with certain known and available wild-type Bt toxins.

Historically, Bt toxin has been used to control populations of pests that damage crops. For example Bt toxin can be topically applied to plants affected by pests as an insecticide. In other cases, plants, such as corn (*Zea mays*), cotton (*Gossypium* sp.), rice (*Oryza sativa* L.), alfalfa (*Medicago sativa*), potato (*Solanum tuberosum*), tomato (*Solanum lycopersicum*), soybean (*Glycine* max), tobacco (*Nicotiana* sp.), canola (*Brassica napus*) and other *Brassica* sp., or other crop plants can be genetically modified to express one or more Bt toxin(s). Thus, in some embodiments, the disclosure provides cells and/or plants and/or seeds comprising a variant Bt toxin or the nucleic acid sequence encoding such a variant, e.g., in the form of a variant Bt toxin expressed from a recombinant nucleic acid encoding a variant Bt toxin provided herein. In some embodiments, the cell is a plant cell. Suitable methods of engineering plant cells and plants to express genes, including wild-type Bt genes, are well known to those of skill in the art, and such methods can be used to produce plant cells and plants expressing the Bt toxin variants provided herein. Additionally, a commodity product produced from such a plant, and comprising a detectable amount of a multifunctional protein as described herein, is also contemplated as an aspect of the invention. Such commodity products may include, without limitation, seeds, fruit, stems, leaves, tubers, or roots of such a plant, optionally further processed to result in, for instance, flour, meal, or oil for consumption by an animal, or for industrial use, for instance as a fuel or lubricant.

Methods for producing a transgenic plant which expresses a nucleic acid segment encoding a novel Bt toxin variant as described herein can be achieved utilizing variations of methods well known in the art. In general, such a method comprises transforming a suitable host cell with a DNA segment which contains a promoter operably linked to a coding region that encodes one or more of the Bt toxin variants. Such a coding region is generally operably linked to a transcription-terminating region, whereby the promoter is capable of driving the transcription of the coding region in the cell, and hence providing the cell the ability to produce the polypeptide in vivo. Vectors, plasmids, cosmids, and DNA segments for use in transforming such cells will generally comprise operons, genes, or gene-derived sequences, either native, or synthetically-derived, and particularly those encoding the disclosed Br toxin variant proteins. These DNA constructs can further include structures such as promoters, enhancers, polylinkers, or other gene sequences which can have regulating activity upon the particular genes of interest. Without limitation, examples of plant transformation vectors include those derived from a Ti plasmid of *Agrobacterium tumefaciens*, as well as those disclosed, e.g., by Herrera-Estrella (*Nature* 303:209-213, 1983). Bevan (Nature 304:184-187, 1983), Klee (*Bio/Technol.* 3:637-642, 1985). Such transgenic plants are desirable for increasing the insecticidal resistance of a monocotyledonous or dicotyledonous plant, by incorporating into such a plant, a transgenic DNA segment encoding one or more Bt toxin variant proteins which are toxic to insects. In a related aspect, the present method also encompasses a seed produced by the transformed plant, a progeny from such seed, and a seed produced by the progeny of the original transgenic plant, produced in accordance with the above process. Such progeny and seeds will have a BR toxin variant protein-encoding transgene stably incorporated into their genome, and such progeny plants expressing the encoded protein would inherit and display the insect control trait or traits afforded by the introduction of such a transgene.

Further aspects of the invention relate to recombinant DNA constructs for expression of a multi-functional pest control protein as herein described. Such a protein may be expressed in a host cell such as a bacterial cell or a plant cell. Recombinant host cells, including bacterial cells and plant cells, comprising such a recombinant construct, are thus also contemplated, as is the multi functional protein produced by the host cell. A resulting protein may be produced for ingestion in the diet of a target pest organism, or by otherwise contacting a target pest, such as a target insect pest, with a multi functional protein as described herein. Topical application of a composition comprising such a multi functional protein is also contemplated. Such application may be performed directly onto a target organism, or the composition may be applied to the environment of a target organism and may thus subsequently contact the organism. Thus such compositions, and methods for producing and formulating such compositions for topical application, are also contemplated. Such a composition may also, for instance, comprise another Bt toxin, as well as one or more other pest control molecule displaying one or more other mode(s) of action (e.g. a chemical active against a target organism of interest).

Examples of techniques for introducing DNA into plant tissue are disclosed in European Patent Application Publication No. 0 289 479, published Nov. 1, 1988, and by Perlak et al. in "Modification of the Coding Sequence Enhances Plant Expression of Insect Control Protein Genes." Proc. Natl. Acad. Sci. USA, 88, pp. 3324-3328 (1991). Examples of methods which can be modified for obtaining transgenic plants that express insect-active proteins include those describing, for example. Cry1A proteins (U.S. Pat. No. 5,880,275), Cry1B (U.S. Patent Application Publication No. 2006/0112447). Cry1C (U.S. Pat. No. 6,033,874), Cry1A/F chimeras (U.S. Pat. Nos. 7,070,982; 6.962.705, and 6.713.063), and a Cry2Ab protein (U.S. Pat. No. 7,064,249).

Phage assisted continuous evolution (PACE) is a particular method for directed evolution that creates and selects for protein variants with a desired activity (Esvelt, et al. *Nature* 472, 499-503, 2011). PACE selects for protein-protein interactions by utilizing engineered *E. coli* and M13 bacteriophage that express a component of a bacterial 2-hybrid system that links the strength of interaction to the fitness of the phage. *E. coli* cells carries two plasmids: the accessory plasmid (AP), which links protein binding to phage propagation and controls selection stringency, and the mutagenesis plasmid (MP), which enables inducible mutagenesis to provide variation. The selection phage (SP) encode an evolving protein that interacts with the target protein and results in the production of pIII, a phage protein required for infectivity of progeny phage. PACE takes place in a fixed-volume vessel that is continuously diluted with fresh host cells. SP encoding protein variants that bind the target propagate faster and become more abundant while SP encoding variants that do not interact with the target propagate at a slower rate and become progressively less abundant. This dynamic prevents the co-evolution of the target and provides continuous selection on the evolving protein.

Certain embodiments of the invention take advantage of recent discoveries enabling modification and insertion of segments directly into the genome of the plant without introduction of a transgene using traditional *Agrobacterium* or ballistic mediated methods, and these are referred to in the art as gene editing and site directed integration. It is within the skill of the art to modify the transgenic DNA present within a transgenic plant. i.e. make modifications for example to a locus within the plant genome that has been introduced and is enabled for the encoding a toxin, and introduce changes into that transgene within the plant. For example, with reference to the embodiments within this application, it is now possible to modify the gene in a cotton plant that expresses a Cry1Ac1 protein, to which any particular lepidopteran target species pest of cotton has developed field resistance, and introduce modifications to the in-planta gene (i.e., edit the gene) that will result in a new nucleotide sequence in the transgene locus that encodes a modified Cry1Ac1 protein that is now capable of binding to a receptor not previously bound by the native Cry1Ac1 in the resistant target species pest of cotton and restore the sensitivity to Cry1Ac1 to the Cry1Ac1 insensitive target species pest. Thus restoring to the transgenic plant the ability to control the pest that has become resistant to the original toxin and to provide two or more modes of action for controlling the pest as a result of the ability of the modified toxin to bind to two or more different receptors. This increases the durability of the plant as well and increases the efficacy of the transgenic plant.

Production of a protein of the present invention in a transgenic plant or plant cell can be combined with means for expressing at least one other gene(s) encoding other protein toxins or pesticidal agents that have been shown to target for control the same or even a different pest. For example, a plant expressing a Bt toxin for controlling a corn earworm may be engineered to contain a modified Bt toxin that binds to two or more different receptors in a corn earworm gut, thus providing for two or more modes of action for controlling a corn earworm pest with a single protein. This engineered plant, if a corn plant, can then be combined with any number of transgenic events known in the art such as MON810. MON89034. MIR162, TC-1507, and the like to provide for an additional Bt toxin effective for controlling corn earworm and other lepidopteran pests of corn. Furthermore, the toxin coding sequences in these events can be engineered to exhibit two or mom modes of action for each of the encoded toxin proteins, such as Cry1Ab. Cry1A.105. Cry2Ab, VIP3Aa and Cry1F. providing for durability and greater efficacy of each of these events in the market place. Such corn plants controlling lepidopteran species can be combined with one or more transgenes that control other pests such as a Coleopteran pest, for instance corn rootworms, exemplified by current commercial transgenic events such as MON88017. DAS-59122-7, and MIR164, which each in turn can be engineered using the methods taught herein to modify the encoded rootworm toxins in each of these embodiments to exhibit two or more modes of action, each such protein binding at least one additional target receptor in a corn rootworm gut to give effect to a more durable product, and to enhance the efficacy of the products as a result of the toxin proteins encoded by these transgenic events to bind to more than one receptor in the target insect gut.

Cells comprising variant Bt toxin can be isolated (i.e., cultured or stored in vitro), or can form part of a plant (e.g., a transgenic plant expressing a variant Bt toxin) or an entire plant, rendering the respective plant resistant to pests susceptible to the variant Bt toxin. Such pests may include, in some embodiments, pests that are resistant or refractory to wild-type Bt toxin.

As used herein, the term “isolated DNA molecule” means that the DNA molecule is present alone or in combination with other compositions but is not within its natural environment. For example, a DNA recombinant molecule comprising a protein-coding sequence and heterologous chloroplast transit peptide sequence is considered isolated when it is found in a context that is not the genome in which it is naturally found. Such a recombinant DNA molecule would be an isolated DNA molecule when present in the genome of a transgenic plant, the components of that recombinant DNA molecule being thus not in their natural environment (that is, the genome of the organism from which the structure was first observed). A recombinant DNA molecule of the invention thus would be an isolated DNA molecule so long as the recombinant DNA molecule was not within the DNA of the organism from which the structure was first observed.

In certain embodiments the present invention also provides a pesticidal protein that comprises a multifunctional variant of Cry1Ac1 (SEQ ID NO:1) selected from the group consisting of Protein 3 (SEQ ID NO:2), Protein 4 (SEQ ID NO:3). Protein 5 (SEQ ID NO:4). The present invention also provides a pesticidal protein that comprises a multifunctional variant of TIC2160 (SEQ ID NO:5), comprising TIC2160* (SEQ ID NO:7).

The present invention also provides a cadherin binding peptide selected from the group consisting of SEQ ID NO:6 and SEQ ID NO:9. These cadherin binding peptides, when inserted into a pesticidal protein, allow for the additional functionality of being able to bind to cadherin receptors in insect cells.

The present invention also provides a pesticidal protein the comprises a multifunctional variant of Cry1Ac1 (SEQ ID NO:1), comprising SEQ ID NO:11. The present invention also provides a pesticidal protein that comprises a multifunctional variant of TIC105 (SEQ ID NO:8), selected from the group consisting of SEQ ID NO:10 and SEQ ID NO:12. The present invention also further provides a chimeric cadherin receptor comprising SEQ ID NO: 13.

EXAMPLES

The function and advantage of these and other embodiments of the present invention will be mom fully understood from the examples described below. The following examples are intended to illustrate the benefits of the present invention and to describe particular embodiments, but are not intended to exemplify the full scope of the invention. Accordingly, it will be understood that the examples are not meant to limit the scope of the invention.

Example 1

PACE Evolved Cry1Ac1 with Additional MOA

A variant CryAc1 protein with an additional mode of action (MOA) was produced by PACE directed evolution (Esvelt, et al. *Nature* 472, 499-503, 2011). The *Bacillus*

*thuringiensis* endotoxin Cry1Ac (SEQ ID NO:1) does not natively bind to the cadherin receptor from the insect pest *Trichoplusia ni* (TnCAD). Badran et al. (*Nature* 533.58-63, 2016) demonstrated that PACE derived variants of Cry1Ac gained affinity for TnCAD. These variants are more toxic to wild-type-Cry1Ac-resistant *T. ni* than wild-type Cry1Ac.

Cultured *Spodoptera frugiperda* (Fall Annyworm. "FAW") Sf9 cells (Vaughn et al., *In Vitro* 13:213-217, 1977), transformed to express selected proteins that act as toxin receptors upon expression in the Sf9 cells and display on the surface of the Sf9 cells, were used to test for binding of various Cry1Ac protein toxin amino acid sequence variants. This binding was compared to binding of the native Cry1Ac toxin protein. Successful binding of a toxin, such as a variant protein, to the surface receptor on the Sf9 cell causes pore formation. The resulting pore allows an added fluorophore to enter the cell via the compromised cell membrane and bind to DNA, causing the cells with pores to fluoresce under appropriate lighting conditions.

Such fluorescence can be compared to background fluorescence levels of appropriate controls, and thus utilized to detect toxin activity. Fluorescence intensity in Sf9 cells expressing any particular receptor to which a variant pesticidal protein may bind is expected to correlate with pesticidal activity.

All amino acid residue substitutions described in this application ae with reference to those positions as set forth above in the Cry1 Ac core toxin amino acid sequence. For instance, for Cry1Ac the core sequence is from residues 29 to 620 in SEQ ID NO:1.

Native (wild-type) Cry1Ac functionally interacts (i.e. binds) with the FAW ABCc2 and ABCc3 transporters, leading to an increased SYTOX® Green (ThermoFisher Scientific, Waltham, MA. USA) fluorescent signal detectable in Sf9 cell cultures expressing those transporters. Native Cry1Ac does not functionally interact with cabbage looper cadherin or soybean looper cadherin. Selected Cry1Ac amino acid sequence variants retain their functional interaction with FAW ABCc2 and ABCc3, while acquiring a new functional interaction with soybean looper cadherin and cabbage looper cadherin.

Cry1Ac1 variants were tested for relative toxicity in insect cell-based assays. Lawns of Sf9 cells, engineered to express cadherin from *T. ni* (cabbage looper. Table 3) or soybean looper (*Chrysodeixis includens* also known as *Pseudoplusia includens*, Table 4), were overlayed with a composition containing cell membrane-impermeable SYTOX® Green dye that fluoresces when it binds with DNA. Cry1Ac amino acid sequence variant proteins were pre-treated with trypsin to release the three-domain Cry1Ac toxic core. The toxicity of Cry1Ac1 and its variants to Sf9 cells expressing *T. ni* (cabbage looper) cadherin, was measured by increased fluorescence intensity of SYTOX® Green dye. Protein concentrations are shown for each toxin. Designated names for certain PACE-evolved variants C02. C03, C05, C09. A01 and A02 (e.g. Badran et al., 2016) are given in Table 1. Each data point is the mean of three measurements, with calculated standard deviation (SD) shown.

Table 1 illustrates the fluorescence intensity caused by presence of Cry1Ac1 and Cry1Ac amino acid sequence variants in Sf9 cells expressing *T. ni* (cabbage looper) cadherin (Table 1A) or *C. includens* (soybean looper) cadherin (Table 1B), as measured by increased relative fluorescence intensity of SYTOX® Green dye. Protein concentrations are shown for each toxin. Cry1 Ac amino acid sequence variants (C02, C03, C05, C09. A01 and A02) were tested. As shown in Tables 1A and 1B, the fluorescence intensity of SYTOX® Green dye utilized to measure toxin-induced cellular pore formation in Sf9 cells expressing these various cadherins and exposed to different variants resulted in increased fluorescence of 2 to 40 times the level of fluorescence compared to control cells using wild type Cry1Ac1 (wt-Cry1Ac1). Thus, certain residues in Cry1Ac can be targeted for modification to obtain a protein toxin that exhibits binding to lepidopteran insect cadherin, which binding results in the protein toxin forming a pore in the membrane that allows the fluorophore to enter the Sf9 cells, bind to cellular DNA, and fluoresce.

TABLE 1A

Fluorescence Intensity of Sf9 cells expressing *T. ni* cadherin Exposed to Cry1Ac amino acid sequence variants.

| | Amino acid substitutions relative to Cry1Ac | Relative fluorescence | Standard deviation |
|---|---|---|---|
| Buffer | | 473 | 22 |
| Empty vector | | 766 | 113 |
| Cry1Ac1, 28 ug/ml | | 549 | 90 |
| Cry1Ac1_D384Y_S404C, 16 ug/ml | D384Y_S404C | 1041 | 61 |
| Cry1Ac1_C02, 7 ug/ml | D384Y_S404C_E461K_N463S_E332G_T304N_A344E_T361I_S582L_F68S_G286D_C15W | 6939 | 120 |
| Cry1Ac1_C03, 4 ug/ml | D384Y_S404C_E461K_N463S_T304N_A344E_T361I_S582L_C15W_M322K_Q353H_F68S_G286D_E332G | 7590 | 455 |
| Cry1Ac1_C05, 9 ug/ml | D384Y_S404C_C15W_T304N_A344E_T361I_E461K_N463S_S582L | 8189 | 708 |
| Cry1Ac1_C09, 3 ug/ml | D384Y_S404C_R198G_S363P_N417D_E332G_E461K_N463S_S582L_T386A | 4929 | 281 |
| Cry1Ac1_A01, 4 ug/ml | D384Y_S404C_E461K_N463S_T304N_A344E_T361I_S582L_C15W_M322K_Q353H | 10591 | 613 |
| Cry1Ac1_A02, 1 ug/ml | D384Y_S404C_R198G_S363P_N417D_E332G_E461K_N463S_S582L | 5425 | 385 |

TABLE 1B

Fluorescence Intensity of Sf9 cells expressing *C. includens* cadherin exposed to Cry1Ac amino acid sequence variants.

| | Amino acid substitutions relative to Cry1Ac | Relative fluorescence | Standard deviation |
|---|---|---|---|
| Buffer | | 546 | 191 |
| Empty vector | | 407 | 70 |
| Cry1Ac1, 28 ug/ml | | 116 | 47 |
| Cry1Ac1_D384Y_S404C, 16 ug/ml | D384Y_S404C | 180 | 115 |
| Cry1Ac1_C02, 7 ug/ml | D384Y_S404C_E461K_N463S_E332G_T304N_A344E_T361I_S582L_F68S_G286D_C15W | 4468 | 697 |
| Cry1Ac1_C03, 4 ug/ml | D384Y_S404C_E461K_N463S_T304N A344E_T361I_S582L_C15W_M322K_Q353H_F68S_G286D_E332G | 3425 | 624 |
| Cry1Ac1_C05, 9 ug/ml | D384Y_S404C_C15W_T304N_A344E_T361I_E461K_N463S_S582L | 3391 | 69 |
| Cry1Ac1_C09, 3 ug/ml | D384Y_S404C_R198G_S363P_N417D_E332G_E461K_N463S_S582L_T386A | 3286 | 649 |
| Cry1Ac1_A01, 4 ug/ml | D384Y_S404C_E461K_N463S_T304N_A344E_T361I_S582L_C15W_M322K_Q353H | 4287 | 572 |
| Cry1Ac1_A02, 1 ug/ml | D384Y_S404C_R198G_S363P_N417D_E332G_E461K_N463S_S582L | 3642 | 284 |

Example 2

The Cry1Ac1 Toxin Variants are Multifunctional, and Retain the Ability to Also Functionally Bind to FAW ABC Transporters Cry1Ac is known to bind to the transporter proteins ABCc2 and ABCc3, which can thus be considered to be receptors for the wild type Cry1Ac protein. Data shown in Table 2A and Table 2B demonstrate how the modifications introduced into the Cry1Ac protein as shown in Tables 1 and 2 affect interaction of variant Cry1Ac with receptors ABCc2 and ABCc3.

The results below show that variants that were tested and compared to wild-type Cry1Ac1 using the Sf9/green dye assay as in Example 1, but with Sf9 cells expressing either FAW ABCc2 or ABCc3 transporter proteins (the insect receptor for wild-type-Cry1Ac1), retained ability to bind to these receptors and induce fluorescent dye uptake. This demonstrates that the various amino acid changes introduced into Cry1Ac1 as shown in Example 1, which provided for Cry1Ac1 binding to the *C. includens* or *T. ni* cadherins, did not result in the loss of function of binding to the FAW receptors. Protein 3 (SEQ ID NO:2) is the _C05 variant protein from Example 1; Protein 4 (SEQ ID NO:3) is the _C03 protein from Example 1, and Protein 5 (SEQ ID NO:4) is the _A01 protein from Example 1; except that, in this example, these polypeptides did not contain the D384Y or the S404C modification which was separately found to cause proteolytic instability in the resulting Cry1Ac1 variant, but which did not result in significant difference in functional activity when used only in bioassay with the Sf9 cell assay.

TABLE 2A

Fluorescence Intensity of Sf9 cells expressing *Spodoptera frugiperda* ABCc2 transporter Exposed to Cry1Ac amino acid sequence variants.

| Toxin | Toxin concentration, ug/ml | Relative fluorescence, mean | Standard deviation |
|---|---|---|---|
| Buffer control | 0 | 4182 | 820 |
| Cry1Ac1 | 0.05 | 58938 | 921 |
| Cry1Ac1 | 0.2 | 82515 | 2377 |
| Cry1Ac1 | 0.5 | 100136 | 1868 |

TABLE 2A-continued

Fluorescence Intensity of Sf9 cells expressing *Spodoptera frugiperda* ABCc2 transporter Exposed to Cry1Ac amino acid sequence variants.

| Toxin | Toxin concentration, ug/ml | Relative fluorescence, mean | Standard deviation |
|---|---|---|---|
| Protein 3 | 0.05 | 68972 | 856 |
| Protein 3 | 0.2 | 87408 | 1100 |
| Protein 3 | 0.5 | 118592 | 6151 |
| Protein 4 | 0.05 | 75437 | 2228 |
| Protein 4 | 0.2 | 94713 | 1501 |
| Protein 4 | 0.05 | 75437 | 2228 |
| Protein 5 | 0.05 | 69133 | 1435 |
| Protein 5 | 0.2 | 86085 | 2642 |
| Protein 5 | 0.5 | 112897 | 2979 |

TABLE 2B

Fluorescence Intensity of Sf9 cells expressing *Spodoptera frugiperda* ABCc3 transporter Exposed to Cry1Ac amino acid sequence variants.

| Toxin | Toxin concentration, ug/ml | Relative fluorescence, mean | Standard deviation |
|---|---|---|---|
| Buffer control | 0 | 11 | 164 |
| Cry1Ac1 | 0.2 | 45252 | 139 |
| Cry1Ac1 | 1 | 92852 | 3978 |
| Cry1Ac1 | 5 | 121659 | 1659 |
| Protein 3 | 0.2 | 24070 | 782 |
| Protein 3 | 1 | 67187 | 1598 |
| Protein 3 | 5 | 115760 | 2671 |
| Protein 4 | 0.2 | 7965 | 66 |
| Protein 4 | 1 | 26474 | 1404 |
| Protein 4 | 5 | 79866 | 1172 |
| Protein 5 | 0.2 | 39769 | 563 |
| Protein 5 | 1 | 84305 | 1372 |
| Protein 5 | 5 | 119408 | 2195 |

Cry1Ac toxin binding to the *S. frugiperda* ABCc2 and ABCc3 transporters is thus retained in the variant toxin proteins and the variants of Cry1Ac retain pore forming ability which allows the fluorophore to accumulate in the Sf9 cells.

Example 3

Cry1Ac1 Variants Exhibiting Two or More Modes of Action (MOA's) on Cabbage Looper Larvae The toxic dose required to kill Cry1Ac1-sensitive loopers and Cry1Ac1-resistant loopers was compared to demonstrate that Cry1Ac1 variants exhibit multiple modes of action (MOA's) on cabbage looper larvae. Provided data also distinguishes between two possible explanations for the observations: that a given Cry1Ac amino acid sequence variant that binds to cadherin may have enhanced affinity to a single receptor, and thus only provides a single mode of action; alternatively, the variant may be binding to two different receptors and therefore would confer two different modes of action for pore forming activity. To distinguish these possibilities, diet bioassays were conducted with *T. ni* larvae of two lines. One line exhibits resistance to Cry1Ac, and the other (wild-type) line is sensitive to Cry1Ac. Larvae were exposed to sucrose gradient purified toxin crystals in a standard diet bioassay (e.g. Baum et al., *J. Econ. Entomol.* 105:616-624, 2012). The results are shown in Table 3.

In Table 3, proteins 1 and 2 correspond to the _C03 and _C05 proteins respectively as shown in Example 1, however as discussed in Example 2, these particular polypeptides contain additional amino acid substitutions (D384Y or the S404C) that may lead to increased proteolysis, and so displayed reduced relative activity in these bioassays. In contrast the corresponding variants that lack these proteolytic instability inducing amino acid substitutions, Protein 4 and Protein 3 respectively (_C03 and _C05 as in Example 1 but lacking D384Y and S404C) as well as Protein 5 (_A01) yield high relative potency scores as shown in Table 3, indicating efficacious binding of the variant Cry1Ac1 to the respective *T. ni* larvae.

TABLE 3

Insecticidal activity of Cry1Ac amino acid sequence variants against Cry1Ac-resistant and susceptible *Trichoplusia ni*.

| | | Toxin | LC50 | 95% CL | Slope | SE | Relative potency (%) |
|---|---|---|---|---|---|---|---|
| Susceptible *T. ni* | Response: Mortality | Cry1Ac | 0.039 | 0.019-0.069 | 2.54 | 0.26 | 100 |
| | | Protein 1 | 0.793 | 0.505-1.082 | 2.84 | 0.41 | 5 |
| | | Protein 2 | 0.715 | 0.407-1.176 | 1.78 | 0.22 | 5 |
| | | Protein 3 | 0.035 | 0.026-0.045 | 3.59 | 0.41 | 111 |
| | | Protein 4 | 0.018 | 0.014-0.020 | 4.68 | 0.75 | 217 |
| | | Protein 5 | 0.021 | 0.015-0.024 | 4.82 | 1.09 | 186 |
| | Response: growth inhibition | Cry1Ac | 0.019 | 0.011-0.027 | 3.09 | 0.39 | 100 |
| | | Protein 1 | 0.136 | 0.110-0.160 | 4.00 | 0.62 | 14 |
| | | Protein 2 | 0.217 | 0.167-0.268 | 2.59 | 0.32 | 9 |
| | | Protein 3 | 0.016 | 0.014-0.018 | 5.53 | 0.82 | 119 |
| | | Protein 4 | 0.007 | 0.003-0.010 | 3.65 | 0.61 | 271 |
| | | Protein 5 | 0.005 | 0.004-0.006 | 4.92 | 0.90 | 380 |
| Cry1Ac resistant *T. ni* | Response: Mortality | Cry1Ac | 51.229 | 9.929-90.241 | 1.89 | 0.36 | 100 |
| | | Protein 1 | 408.713 | 263.629- | 0.81 | 0.10 | 13 |
| | | Protein 2 | 235.698 | 79.467-510.323 | 1.12 | 0.15 | 22 |
| | | Protein 3 | 1.938 | 1.550-2.352 | 2.55 | 0.29 | 2643 |
| | | Protein 4 | 1.841 | 1.390-2.312 | 2.25 | 0.28 | 2783 |
| | | Protein 5 | 0.153 | 0.046-0.289 | 2.01 | 0.22 | 33483 |
| | Response: growth inhibition | Cry1Ac | 23.402 | 4.587-46.512 | 1.49 | 0.25 | 100 |
| | | Protein 1 | 56.626 | 40.600-75.685 | 1.84 | 0.21 | 41 |
| | | Protein 2 | 47.232 | 20.236-90.729 | 1.16 | 0.12 | 50 |
| | | Protein 3 | 1.116 | 0.797-1.484 | 2.19 | 0.23 | 2097 |
| | | Protein 4 | 0.733 | 0.515-0.949 | 2.06 | 0.28 | 3193 |
| | | Protein 5 | 0.083 | 0.061-0.104 | 2.57 | 0.38 | 28195 |

Results of diet bioassay with *T. ni* (Table 3) illustrate the activity (mortality and growth inhibition) of Cry1Ac1 variants (utilized as sucrose gradient purified Bi crystals) in diet bioassay compared to native Cry1Ac. The LC50 data for the Cry1Ac susceptible cabbage looper larvae indicate that the proteins have been engineered to exhibit a second mode of action. A decrease in apparent activity seen for proteins 3-5 on resistant *T. ni*, as compared to susceptible *T. ni*, may be explained as due to binding to only a single receptor in the resistant insect cells, whereas for Cry1Ac1-susceptible *T. ni* the toxin is binding at least two different receptors, resulting in differences in effective dose on the different *T. ni* lines.

The LC50 range for the engineered Cry1Ac amino acid sequence variants is 0.018-0.025 on the Cry1Ac susceptible *T. ni* colony and 0.153-1.938 on the Cry1Ac resistant colony. This data is consistent with the presence of multiple modes of action in the engineered proteins. i.e. there are n MOA's available in the susceptible colony in the presence of the Cry1Ac amino acid sequence variants (the colony that is sensitive to the wild type Cry1Ac), and there are n−1 MOA's available in the resistant colony in the presence of the Cry1Ac amino acid sequence variants (the colony that has evolved resistance to the wild type Cry1Ac). The data also suggests that a pesticidal protein that acts to confer its effects upon a target pest by binding to two or more different receptors in that pest may provide for the delivery of a decreased minimum effective dose when both receptors are present. Such proteins can confer upon a plant producing a pesticidally effective amount of the pesticidal protein the ability to deliver a more efficacious dose to any particular susceptible target pest, and to provide a more durable form of insect control because the protein is providing its effects through multiple modes of action and it will be less likely that any single pest would become resistant to the more than one mode of action conferred by the protein.

Example 4

Modifying TIC2160 to Provide a Additional Mode of Action

Lepidopteran active toxin TIC2160 (SEQ ID NO:5), lacks substantial insecticidal or insect growth-inhibiting activity when tested in bioassay against fall armyworm larvae. However, it is demonstrated herein that, by introducing a peptide sequence, selected for its ability to bind with high affinity to the Sf cadherin, into domain IV of the TIC2160 protein, an increased activity of the modified TIC2160 protein is seen. The modified TIC2160 protein thus displays an additional mode of action.

TIC2160 is an insect control protein that is toxic to a number of Lepidopteran species, and is derived from a *Bacillus* species (PCT/US2015/055802). However, this protein displays little activity when tested against fall armyworms in laboratory bioassays.

A Sf cadherin protein (Sf CAD) was isolated and a specific 12 amino acid segment that demonstrated tight binding to Sf CAD was identified. Introgression of the 12-mer segment into the TIC2160 protein structure at several predicted loop regions within the TIC2160 protein was performed, and the resulting candidate molecules were tested for their ability to maintain lepidopteran specific toxic properties. A location in Domain IV of the TIC2160 protein was identified that supported the introgression of the 12-mer amino acid sequence NH3-Val-Asp-Trp-Trp-Ser-Pro-Phe-Tyr-Asp-Arg-Leu-Lys-COOH (SEQ ID NO:6). The resulting protein TIC2160* (SEQ ID NO:7) was tested at 250 ppm in diet bioassays against Sf larvae. The diet bioassay was evaluated to measure the effect of a toxin on insect growth, or decreased growth (stunting). 20 to 30 insects were evaluated in each dosing group (or control group); insect size was evaluated after one week on the diet with or without toxin added. Size was evaluated as the number of pixels generated per insect using a high resolution digital camera image. Larvae that received empty vector control or untreated control were not stunted. A positive control lepidopteran active protein known for bioactivity against Sf and also tested at 250 ppm showed about 55% stunting relative to controls. The unmodified wild type TIC2160 exhibited about 25% stunting, and the TIC2160* proteins all exhibited about 80-85% stunting. Thus inclusion of the twelve amino acid peptide into Domain IV of the TIC2160 protein provided a new mode of action for this protein with respect to Sf larvae.

Example 5

Modifying Additional Lepidopteran Active Toxins to Provide an Additional Mode of Action Modification of lepidopteran active toxins TIC105 (SEQ ID NO:8; see U.S. Pat. No. 8,034,997, referred to therein as Cry1A.105) and Cry1Ac1 (SEQ ID NO:1) was also performed.

*S. frugiperda* Sf9 cells in culture were transformed with proteins that act as toxin receptors, to test for binding of various Cry1Ac and TIC105 protein toxin amino acid sequence variants. Binding of such modified proteins was compared to that of the native Cry1Ac (SEQ ID NO:1) and TIC105 (SEQ ID NO:8) toxin protein. As noted above the binding of a modified toxin to the surface receptor on the Sf9 cell causes pore formation; the resulting pore allows a fluorophore to enter the insect cell and the cells can display increased fluoresce under the appropriate lighting conditions. Resulting fluorescence can be compared to background fluorescence of control cells. All amino acid residue insertions-replacements referenced in this application are with reference to those positions as set forth above in the Cry1Ac and TIC105 toxin amino acid sequence.

Cry1Ac and TIC105 display a functional interaction with the *S. frugiperda* ABCc2 transporter leading to an increased SYTOX® Green dye fluorescence signal in Sf9 cells expressing those transporters. Cry1Ac and TIC105 do not display a natural functional interaction with *S. frugiperda* cadherin. Cry1Ac and TIC105 amino acid sequence variants, created by inserting a peptide sequence that binds to *S. frugiperda* cadherin into Cry1Ac and TIC105 scaffolds, retain their functional interaction with FAW ABCc2. Further, some variants acquire new functional interaction with *S. frugiperda* cadherin. Fluorescence intensity in Sf9 cells expressing any particular receptor to which a pesticidal protein will bind is expected to correlate with pesticidal activity.

Cry1Ac1 and TIC105 *S. frugiperda* binding variants were tested for relative toxicity in insect cell-based assays. Lawns of Sf9 cells, engineered to express cadherin from *S. frugiperda* were overlayed with a composition containing membrane-impermeable SYTOX® Green dye and Cry1Ac- or TIC105-amino acid sequence variants, pretreated with trypsin to release the three-domain toxic core (for Cry1Ac the core is from residues 29 to 620 in SEQ ID NO:1; for TIC105 the core is from residues 29 to 619 in SEQ ID NO:8). Variants which bind to cadherin receptors aggregate to form pores, allowing the dye to enter the compromised cell membrane. The dye can then bind to DNA and result in intense green fluorescence. The toxicity of Cry1Ac1, TIC105 and its variants to Sf9 cells expressing *S. frugiperda* cadherin was inferred by increased fluorescence intensity of SYTOX® Green dye.

The TIC105 variant of SEQ ID NO:10 comprises the Sf cadherin binding protein of SEQ ID NO:9 inserted into the TIC105 scaffold (SEQ ID NO:8), in place of the three residues from G342 to A344. Testing this variant in cells expressing *S. frugiperda* cadherin demonstrated that addition of *S. frugiperda* cadherin binding peptide (SEQ ID NO:9) resulted in increased fluorescence intensity of approximately 4 times the level of fluorescence seen with control cells using wild type unmodified TIC105 (SEQ ID NO:8). At the same time the TIC105 variant (SEQ ID NO:10) was as active as wild-type unmodified TIC105 (SEQ ID NO:8) against cells expressing FAW ABCc2 receptor.

The Cry1Ac1 variant in SEQ ID NO:11, comprises the Sf cadherin binding protein of SEQ ID NO:6 inserted into the Cry1Ac1 scaffold (SEQ ID NO:1), following residue N343. Testing this variant in cells expressing *S. frugiperda* cadherin showed that addition of *S. frugiperda* cadherin binding peptide (SEQ ID NO:6) resulted in increased fluorescence intensity of 4 to 5 times the level of fluorescence compared to control cells using wild type unmodified Cry1Ac1 (SEQ ID NO:1). At the same time the Cry1Ac1 variant (SEQ ID NO:10) was as active as wild type unmodified TIC105 (SEQ ID NO:8) against cells expressing FAW ABCc2 receptor. Thus the TIC105 and Cry1Ac1 toxin variants, comprising SEQ ID NOs:10 or 11, am multifunctional toxins engineered to be effective against cells expressing Sf cadherin while retaining activity against cells expressing the Sf ABCc2 transporter.

Example 6

PACE Evolved TIC105 with Additional MOA

TIC105 (SEQ ID NO:8), a chimera toxin of Cry1Ab-1Ab-1Fa binds to the transporter proteins FAW ABCc2 and APN1/ABCc3, considered to be receptors for the wild-type TIC105 protein. TIC105 does not bind the cadherin receptor of *S. frugiperda* (SfCAD) but does bind the cadherin receptor of *Helicoverpa zea* (HzCAD). The protein variants described here were first selected using PACE (see Example 1) with an SP encoding TIC105 and host cells with an AP expressing a chimeric cadherin of *S. frugiperda* and *H. zea* (Sf/HzCAD). Following the first round of PACE on Sf/HzCAD, variant SPs were evolved in two additional rounds of evolution on SfSCAD.

TIC105 and its variants were tested for relative toxicity in insect cell-based assays. The toxicity to Sf9 cells expressing chimera Ci/Sf/Ci.Cadherin (SEQ ID NO:13) from *S. frugiperda* (fall armyworm) and C. *includens* (soybean looper), was measured by increased fluorescence intensity of SYTOX® Green nucleic acid stain. TIC105 amino acid sequence variants were pre-treated with trypsin to release the three-domain TIC105 toxic core (residues 29-619). TIC105 and its variants were tested in an insect cell-based assay. Each data point was the mean of three measurements subtracted from beta-glucanase background, with calculated standard deviation (SD) shown. PACE derived TIC105 variant IS0349 (SEQ ID NO:12) showed a relative fluorescence of 12705 (SD: 2892) compared to a value for unmodified TIC105 of −1229 (SD: 1349), indicating that the evolved toxin bound to the expressed cadherin.

To determine whether the modifications introduced into TIC105 variant IS0349 (SEQ ID NO:12) resulted in a loss of function relative to the ability of the modified TIC105 to bind normally to receptor *S. frugiperda* ABCc2, TIC105 and variants were also tested against Sf9 cells expressing the SfABCc2 transporter. PACE derived TIC105 variant IS0349 (SEQ ID NO:12) showed a relative fluorescence of 92513 (SD: 6571) compared to a value for unmodified TIC105 of 57201 (SD: 13372), indicating that binding to its natural receptor was retained by the polypeptides comprising the PACE-induced mutations.

Additional advantages and modifications of the examples will readily occur to those of ordinary skill in the art. The invention in its broader aspects is not limited to the specific details and representative embodiments shown in and described herein. Accordingly, various modifications may be made to the examples without departing from the spirit and scope of the general inventive concepts described.

SEQUENCE LISTING

```
Sequence total quantity: 13
SEQ ID NO: 1           moltype = AA  length = 1178
FEATURE                Location/Qualifiers
source                 1..1178
                       mol_type = protein
                       organism = Bacillus thuringiensis
SEQUENCE: 1
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLFAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNIIASDS ITQIPAVKGN  480
FLFNGSVISG PGFTGGDLVR LNSSGNNIQN RGYIEVPIHF PSTSTRYRVR VRYASVTPIH  540
LNVNWGNSSI FSNTVPATAT SLDNLQSSDF GYFESANAFT SSLGNIVGVR NFSGTAGVII  600
DRFEFIPVTA TLEAEYNLER AQKAVNALFT STNQLGLKTN VTDYHIDQVS NLVTYLSDEF  660
CLDEKRELSE KVKHAKRLSD ERNLLQDSNF KDINRQPERG WGGSTGITIQ GGDDVFKENY  720
VTLSGTFDEC YPTYLYQKID ESKLKAFTRY QLRGYIEDSQ DLEIYLIRYN AKHETVNVPG  780
TGSLWPLSTQ SPIGKCGEPN RCAPHLEWNP DLDCSCRDGE KCAHHSHHFS LDIDVGCTDL  840
NEDLGVWVIF KIKTQDGHAR LGNLEFLEEK PLVGEALARV KRAEKKWRDK REKLEWETNI  900
VYKEAKESVD ALFVNSQYDQ LQADTNIAMI HAADKRVHSI REAYLPELSV IPGVNAAIFE  960
ELEGRIFTAF SLYDARNVIK NGDFNNGLSC WNVKGHVDVE EQNNQRSVLV VPEWEAEVSQ  1020
EVRVCPGRGY ILRVTAYKEG YGEGCVTIHE IENNTDELKF SNCVEEEIYP NNTVTCNDYT  1080
```

-continued

```
VNQEEYGGAY TSRNRGYNEA PSVPADYASV YEEKSYTDGR RENPCEFNRG YRDYTPLPVG  1140
YVTKELEYFP ETDKVWIEIG ETEGTFIVDS VELLLMEE                          1178

SEQ ID NO: 2            moltype = AA  length = 1178
FEATURE                 Location/Qualifiers
source                  1..1178
                        mol_type = protein
                        note = synthetic
                        organism = synthetic construct
SEQUENCE: 2
MDNNPNINEC IPYNWLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLFAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSINIYTDAH RGYYYWSGHQ IMASPVGFSG PEFTFPLYGT MGNEAPQQRI VAQLGQGVYR  360
ILSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA KFSNIIASDS ITQIPAVKGN  480
FLFNGSVISG PGFTGGDLVR LNSSGNNIQN RGYIEVPIHF PSTSTRYRVR VRYASVTPIH  540
LNVNWGNSSI FSNTVPATAT SLDNLQSSDF GYFESANAFT SLLGNIVGVR NFSGTAGVII  600
DRFEFIPVTA TLEAEYNLER AQKAVNALFT STNQLGLKTN VTDYHIDQVS NLVTYLSDEF  660
CLDEKRELSE KVKHAKRLSD ERNLLQDSNF KDINRQPERG WGGSTGITIQ GGDDVFKENY  720
VTLSGTFDEC YPTYLYQKID ESKLKAFTRY QLRGYIEDSQ DLEIYLIRYN AKHETVNVPG  780
TGSLWPLSAQ SPIGKCGEPN RCAPHLEWNP DLDCSCRDGE KCAHHSHHFS LDIDVGCTDL  840
NEDLGVWVIF KIKTQDGHAR LGNLEFLEEK PLVGEALARV KRAEKKWRDK REKLEWETNI  900
VYKEAKESVD ALFVNSQYDQ LQADTNIAMI HAADKRVHSI REAYLPELSV IPGVNAAIFE  960
ELEGRIFTAF SLYDARNVIK NGDFNNGLSC WNVKGHVDVE EQNNQRSVLV VPEWEAEVSQ  1020
EVRVCPGRGY ILRVTAYKEG YGEGCVTIHE IENNTDELKF SNCVEEEIYP NNTVTCNDYT  1080
VNQEEYGGAY TSRNRGYNEA PSVPADYASV YEEKSYTDGR RENPCEFNRG YRDYTPLPVG  1140
YVTKELEYFP ETDKVWIEIG ETEGTFIVDS VELLLMEE                          1178

SEQ ID NO: 3            moltype = AA  length = 1178
FEATURE                 Location/Qualifiers
source                  1..1178
                        mol_type = protein
                        note = synthetic
                        organism = synthetic construct
SEQUENCE: 3
MDNNPNINEC IPYNWLSNPE VEVLGGERIE TGYTPIDISL SLTQFLLSEF VPGAGFVLGL  60
VDIIWGISGP SQWDAFLVQI EQLINQRIEE FARNQAISRL EGLSNLYQIY AESFREWEAD  120
PTNPALREEM RIQFNDMNSA LTTAIPLFAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQDIERS IRSPHLMDIL  300
NSINIYTDAH RGYYYWSGHQ IKASPVGFSG PGFTFPLYGT MGNEAPQQRI VAHLGQGVYR  360
ILSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA KFSNIIASDS ITQIPAVKGN  480
FLFNGSVISG PGFTGGDLVR LNSSGNNIQN RGYIEVPIHF PSTSTRYRVR VRYASVTPIH  540
LNVNWGNSSI FSNTVPATAT SLDNLQSSDF GYFESANAFT SLLGNIVGVR NFSGTAGVII  600
DRFEFIPVTA TLEAEYNLER AQKAVNALFT STNQLGLKTN VTDYHIDQVS NLVTYLSDEF  660
CLDEKRELSE KVKHAKRLSD ERNLLQDSNF KDINRQPERG WGGSTGITIQ GGDDVFKENY  720
VTLSGTFDEC YPTYLYQKID ESKLKAFTRY QLRGYIEDSQ DLEIYLIRYN AKHETVNVPG  780
TGSLWPLSAQ SPIGKCGEPN RCAPHLEWNP DLDCSCRDGE KCAHHSHHFS LDIDVGCTDL  840
NEDLGVWVIF KIKTQDGHAR LGNLEFLEEK PLVGEALARV KRAEKKWRDK REKLEWETNI  900
VYKEAKESVD ALFVNSQYDQ LQADTNIAMI HAADKRVHSI REAYLPELSV IPGVNAAIFE  960
ELEGRIFTAF SLYDARNVIK NGDFNNGLSC WNVKGHVDVE EQNNQRSVLV VPEWEAEVSQ  1020
EVRVCPGRGY ILRVTAYKEG YGEGCVTIHE IENNTDELKF SNCVEEEIYP NNTVTCNDYT  1080
VNQEEYGGAY TSRNRGYNEA PSVPADYASV YEEKSYTDGR RENPCEFNRG YRDYTPLPVG  1140
YVTKELEYFP ETDKVWIEIG ETEGTFIVDS VELLLMEE                          1178

SEQ ID NO: 4            moltype = AA  length = 1178
FEATURE                 Location/Qualifiers
source                  1..1178
                        mol_type = protein
                        note = synthetic
                        organism = synthetic construct
SEQUENCE: 4
MDNNPNINEC IPYNWLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLFAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSINIYTDAH RGYYYWSGHQ IKASPVGFSG PEFTFPLYGT MGNEAPQQRI VAHLGQGVYR  360
ILSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA KFSNIIASDS ITQIPAVKGN  480
FLFNGSVISG PGFTGGDLVR LNSSGNNIQN RGYIEVPIHF PSTSTRYRVR VRYASVTPIH  540
LNVNWGNSSI FSNTVPATAT SLDNLQSSDF GYFESANAFT SLLGNIVGVR NFSGTAGVII  600
DRFEFIPVTA TLEAEYNLER AQKAVNALFT STNQLGLKTN VTDYHIDQVS NLVTYLSDEF  660
CLDEKRELSE KVKHAKRLSD ERNLLQDSNF KDINRQPERG WGGSTGITIQ GGDDVFKENY  720
VTLSGTFDEC YPTYLYQKID ESKLKAFTRY QLRGYIEDSQ DLEIYLIRYN AKHETVNVPG  780
```

```
TGSLWPLSAQ SPIGKCGEPN RCAPHLEWNP DLDCSCRDGE KCAHHSHHFS LDIDVGCTDL  840
NEDLGVWVIF KIKTQDGHAR LGNLEFLEEK PLVGEALARV KRAEKKWRDK REKLEWETNI  900
VYKEAKESVD ALFVNSQYDQ LQADTNIAMI HAADKRVHSI REAYLPELSV IPGVNAAIFE  960
ELEGRIFTAF SLYDARNVIK NGDFNNGLSC WNVKGHVDVE EQNNQRSVLV VPEWEAEVSQ  1020
EVRVCPGRGY ILRVTAYKEG YGEGCVTIHE IENNTDELKF SNCVEEEIYP NNTVTCNDYT  1080
VNQEEYGGAY TSRNRGYNEA PSVPADYASV YEEKSYTDGR RENPCEFNRG YRDYTPLPVG  1140
YVTKELEYFP ETDKVWIEIG ETEGTFIVDS VELLLMEE                         1178

SEQ ID NO: 5            moltype = AA  length = 798
FEATURE                 Location/Qualifiers
source                  1..798
                        mol_type = protein
                        organism = Bacillus thuringiensis
SEQUENCE: 5
MQRMIIVDNN KLNVRALPSF IDYFNGIYGF ATGIKDIMGM IFKTDTGGSN LTLDEILKNQ  60
NLLNDISGKL DGINGDLGDL IAQGNLNSEL AKELLKISNE QNQMLNHVNA QLNAINSTLN  120
IYLPKITSML NEVMKQNHVL SLQIEFLSKQ LQEISDKLDI INLNVLINST LTEITPAYQR  180
IKYVNEKFDE LTSTVEKNPK SYQDNVTKEV IENLNELTEL AKSVTKNDMD SFEFYLQTFH  240
DVMTGNNLFG RSALKTASEL ITKENVTTRG SEIGKVYNFL IVLTSLQAKA FLTLTACRKL  300
LGLTDIDYTQ IMNHHIDGQK REFRINILPT LSNNFSNPSY SKNRGSDIDD PIVVLEAAPG  360
YALIGFEILN DPLPILKGYQ ARLKPNYQVD RESMSETIYG DIHKLFCPKQ LEQKYYIKDI  420
EFPEGYVITK IVFEKRLNQL GYEVTANFYD PSTGSIDLNK VKVESWKEKS CEEDSCEDEY  480
SIIKAETDGI YMPLGVVSET FLTPIYGFGL TVDEKNQKIT LTGKSYLRES LLETDLLNNE  540
TYLIASPDGY ISSIVENWNI TSDNTGSWRA NNNNAFVDKA DTIKGSSSLY THKDGEFSQF  600
IGNKLKPKTN YVIQYVIKGR PAIYLKNNKD TLFEDTKNNF SDFQTVTKKF NSGVNPSEIY  660
FLFKNQSEYE AWGNNFIILE IKSLEFLPQM LKPEDWIPSG NVQMKDGGRL EILGDGYFKQ  720
FIKLENDSTY HLRLSVKGTG RVSIIDESKY LLFVNVKDED LTRVIKNTSS KGECFIALEG  780
TYVENSSTIF SNVSIVKE                                               798

SEQ ID NO: 6            moltype = AA  length = 12
FEATURE                 Location/Qualifiers
source                  1..12
                        mol_type = protein
                        note = synthetic
                        organism = synthetic construct
SEQUENCE: 6
VDWWSPFYDR LK                                                     12

SEQ ID NO: 7            moltype = AA  length = 807
FEATURE                 Location/Qualifiers
source                  1..807
                        mol_type = protein
                        note = synthetic
                        organism = synthetic construct
SEQUENCE: 7
MQRMIIVDNN KLNVRALPSF IDYFNGIYGF ATGIKDIMGM IFKTDTGGSN LTLDEILKNQ  60
NLLNDISGKL DGINGDLGDL IAQGNLNSEL AKELLKISNE QNQMLNHVNA QLNAINSTLN  120
IYLPKITSML NEVMKQNHVL SLQIEFLSKQ LQEISDKLDI INLNVLINST LTEITPAYQR  180
IKYVNEKFDE LTSTVEKNPK SYQDNVTKEV IENLNELTEL AKSVTKNDMD SFEFYLQTFH  240
DVMTGNNLFG RSALKTASEL ITKENVTTRG SEIGKVYNFL IVLTSLQAKA FLTLTACRKL  300
LGLTDIDYTQ IMNHHIDGQK REFRINILPT LSNNFSNPSY SKNRGSDIDD PIVVLEAAPG  360
YALIGFEILN DPLPILKGYQ ARLKPNYQVD RESMSETIYG DIHKLFCPKQ LEQKYYIKDI  420
EFPEGYVITK IVFEKRLNQL GYEVTANFYD PSTGSIDLNK VKVESWKEKS CEEDSCEDEY  480
SIIKAETDGI YMPLGVVSET FLTPIYGFGL TVDEKNQKIT LTGKSYLRES LLETDLLNNE  540
TYLIASPDGY ISSIVENWNI TSDNTGSWRA NNNNAFVDKA DTIKGSSSLY THKDGEFSQF  600
IGNKLKPKTN YVIQYVIKGR PAIYLKNNKD TLFEDTKNNF SDFQTVTKKF NSGVNPSEIY  660
FLFKNQSEYE AWGNNFIILE IKSLEFLPQM LKPEDWIPSG NVQMKDGGRL EILGDGYFKQ  720
FIKLENDSTY HLRLSVKGTG RVSIIDVDWW SPFYDRLKYL LFVNVKDEDL TRVIKNTSSK  780
GECFIALEGT YVENSSTIFS NVSIVKE                                     807

SEQ ID NO: 8            moltype = AA  length = 1177
FEATURE                 Location/Qualifiers
source                  1..1177
                        mol_type = protein
                        note = synthetic
                        organism = synthetic construct
SEQUENCE: 8
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLFAV QNYQVPLLSV YVQAANLHLS VLRDVSVFGQ  180
RWGFDAATIN SRYNDLTRLI GNYTDHAVRW YNTGLERVWG PDSRDWIRYN QFRRELTLTV  240
LDIVSLFPNY DSRTYPIRTV SQLTREIYTN PVLENFDGSF RGSAQGIEGS IRSPHLMDIL  300
NSITIYTDAH RGEYYWSGHQ IMASPVGFSG PEFTFPLYGT MGNAAPQQRI VAQLGQGVYR  360
TLSSTLYRRP FNIGINNQQL SVLDGTEFAY GTSSNLPSAV YRKSGTVDSL DEIPPQNNNV  420
PPRQGFSHRL SHVSMFRSGF SNSSVSIIRA PMFSWIHRSA EFNNIIASDS ITQIPLVKAH  480
TLQSGTTVVR GPGFTGGDIL RRTSGGPFAY TIVNINGQLP QRYRARIRYA STTNLRIYVT  540
VAGERIFAGQ FNKTMDTGDP LTFQSFSYAT INTAFTFPMS QSSFTVGADT FSSGNEVYID  600
RFELIPVTAT LEAEYNLERA QKAVNALFTS TNQLGLKTNV TDYHIDQVSN LVTYLSDEFC  660
LDEKRELSEK VKHAKRLSDE RNLLQDSNFK DINRQPERGW GGSTGITIQG GDDVFKENYV  720
```

-continued

```
TLSGTFDECY PTYLYQKIDE SKLKAFTRYQ LRGYIEDSQD LEIYSIRYNA KHETVNVPGT  780
GSLWPLSAQS PIGKCGEPNR CAPHLEWNPD LDCSCRDGEK CAHHSHHFSL DIDVGCTDLN  840
EDLGVWVIFK IKTQDGHARL GNLEFLEEKP LVGEALARVK RAEKKWRDKR EKLEWETNIV  900
YKEAKESVDA LFVNSQYDQL QADTNIAMIH AADKRVHSIR EAYLPELSVI PGVNAAIFEE  960
LEGRIFTAFS LYDARNVIKN GDFNNGLSCW NVKGHVDVEE QNNQRSVLVV PEWEAEVSQE  1020
VRVCPGRGYI LRVTAYKEGY GEGCVTIHEI ENNTDELKFS NCVEEEIYPN NTVTCNDYTV  1080
NQEEYGGAYT SRNRGYNEAP SVPADYASVY EEKSYTDGRR ENPCEFNRGY RDYTPLPVGY  1140
VTKELEYFPE TDKVWIEIGE TEGTFIVDSV ELLLMEE                           1177

SEQ ID NO: 9            moltype = AA  length = 12
FEATURE                 Location/Qualifiers
source                  1..12
                        mol_type = protein
                        note = synthetic
                        organism = synthetic construct
SEQUENCE: 9
SDYGWWRPFQ PG                                                      12

SEQ ID NO: 10           moltype = AA  length = 1186
FEATURE                 Location/Qualifiers
source                  1..1186
                        mol_type = protein
                        note = synthetic
                        organism = synthetic construct
SEQUENCE: 10
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLFAV QNYQVPLLSV YVQAANLHLS VLRDVSVFGQ  180
RWGFDAATIN SRYNDLTRLI GNYTDHAVRW YNTGLERVWG PDSRDWIRYN QFRRELTLTV  240
LDIVSLFPNY DSRTYPIRTV SQLTREIYTN PVLENFDGSF RGSAQGIEGS IRSPHLMDIL  300
NSITIYTDAH RGEYYWSGHQ IMASPVGFSG PEFTFPLYGT MSDYGWWRPF QPGAPQQRIV  360
AQLGQGVYRT LSSTLYRRPF NIGINNQQLS VLDGTEFAYG TSSNLPSAVY RKSGTVDSLD  420
EIPPQNNNVP PRQGFSHRLS HVSMFRSGFS NSSVSIIRAP MFSWIHRSAE FNNIIASDSI  480
TQIPLVKAHT LQSGTTVVRG PGFTGGDILR RTSGGPFAYT IVNINGQLPQ RYRARIRYAS  540
TTNLRIYVTV AGERIFAGQF NKTMDTGDPL TFQSFSYATI NTAFTFPMSQ SSFTVGADTF  600
SSGNEVYIDR FELIPVTATL EAEYNLERAQ KAVNALFTST NQLGLKTNVT DYHIDQVSNL  660
VTYLSDEFCL DEKRELSEKV KHAKRLSDER NLLQDSNFKD INRQPERGWG GSTGITIQGG  720
DDVFKENYVT LSGTFDECYP TYLYQKIDES KLKAFTRYQL RGYIEDSQDL EIYSIRYNAK  780
HETVNVPGTG SLWPLSAQSP IGKCGEPNRC APHLEWNPDL DCSCRDGEKC AHHSHHFSLD  840
IDVGCTDLNE DLGVWVIFKI KTQDGHARLG NLEFLEEKPL VGEALARVKR AEKKWRDKRE  900
KLEWETNIVY KEAKESVDAL FVNSQYDQLQ ADTNIAMIHA ADKRVHSIRE AYLPELSVIP  960
GVNAAIFEEL EGRIFTAFSL YDARNVIKNG DFNNGLSCWN VKGHVDVEEQ NNQRSVLVVP  1020
EWEAEVSQEV RVCPGRGYIL RVTAYKEGYG EGCVTIHEIE NNTDELKFSN CVEEEIYPNN  1080
TVTCNDYTVN QEEYGGAYTS RNRGYNEAPS VPADYASVYE EKSYTDGRRE NPCEFNRGYR  1140
DYTPLPVGYV TKELEYFPET DKVWIEIGET EGTFIVDSVE LLLMEE                 1186

SEQ ID NO: 11           moltype = AA  length = 1190
FEATURE                 Location/Qualifiers
source                  1..1190
                        mol_type = protein
                        note = synthetic
                        organism = synthetic construct
SEQUENCE: 11
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLFAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGSAQGIERS IRSPHLMDIL  300
NSITIYTDAH RGYYYWSGHQ IMASPVGFSG PEFTFPLYGT MGNVDWWSPF YDRLKAAPQQ  360
RIVAQLGQGV YRTLSSTLYR RPFNIGINNQ QLSVLDGTEF AYGTSSNLPS AVYRKSGTVD  420
SLDEIPPQNN NVPPRQGFSH RLSHVSMFRS GFSNSSVSII RAPMFSWIHR SAEFNNIIAS  480
DSITQIPAVK GNFLFNGSVI SGPGFTGGDL VRLNSSGNNI QNRGYIEVPI HFPSTSTRYR  540
VRVRYASVTP IHLNVNWGNS SIFSNTVPAT ATSLDNLQSS DFGYFESANA FTSSLGNIVG  600
VRNFSGTAGV IIDRFEFIPV TATLEAEYNL ERAQKAVNAL FTSTNQLGLK TNVTDYHIDQ  660
VSNLVTYLSD EFCLDEKREL SEKVKHAKRL SDERNLLQDS NFKDINRQPE RGWGGSTGIT  720
IQGGDDVFKE NYVTLSGTFD ECYPTYLYQK IDESKLKAFT RYQLRGYIED SQDLEIYLIR  780
YNAKHETVNV PGTGSLWPLS AQSPIGKCGE PNRCAPHLEW NPDLDCSCRD GEKCAHHSHH  840
FSLDIDVGCT DLNEDLGVWV IFKIKTQDGH ARLGNLEFLE EKPLVGEALA RVKRAEKKWR  900
DKREKLEWET NIVYKEAKES VDALFVNSQY DQLQADTNIA MIHAADKRVH SIREAYLPEL  960
SVIPGVNAAI FEELEGRIFT AFSLYDARNV IKNGDFNNGL SCWNVKGHVD VEEQNNQRSV  1020
LVVPEWEAEV SQEVRVCPGR GYILRVTAYK EGYGEGCVTI HEIENNTDEL KFSNCVEEEI  1080
YPNNTVTCND YTVNQEEYGG AYTSRNRGYN EAPSVPADYA SVYEEKSYTD GRRENPCEFN  1140
RGYRDYTPLP VGYVTKELEY FPETDKVWIE IGETEGTFIV DSVELLLMEE             1190

SEQ ID NO: 12           moltype = AA  length = 1177
FEATURE                 Location/Qualifiers
source                  1..1177
                        mol_type = protein
                        note = synthetic
```

-continued

```
                        organism = synthetic construct
SEQUENCE: 12
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLFAV QNYQVPLLSV YVQAANLHLS VLRDVSVFGQ  180
RWGFDAATIN SRYNDLTRLI GNYTDHAVRW YNTGLERVWG PDSRDWIRYN QFRRELTLTV  240
LDIVSLFPNY DSRTYPIRTV SQLTREIYTN PVLENFDGSF RGSAQGIEGS IRSPHLMDIL  300
NSITIYTDAH RGEYYWSGHQ IMASPVGYSG PEFTFPLYGT MGNAAPQQRI VAQLGQGVYR  360
TLSSTLYRRP FNIGINNQQL SVLDGTEFAY GTSSNLPSAV YRKIGTVDSL DEIPPQNNNV  420
PPRQGFSHRL SHVSMFRSGF SNSSVSIIRA PMFSWIHRSA GFCNIIRGDS ITQIPLVKAY  480
ALHSGTTVVR GPGFTGGDIL RRTSGGPFAC TIVNINGQLP QRYCARIRYA STTNLRIYVT  540
VAGERIFAGQ FNKTMNTGDP LTFQSFSYAT INTAFTFPMR QSSFTVGADT FSSGNEVYID  600
RFELIPVAAT LQAEYDLERA QKAVNALFTS TNQLGLKTNV TDYHIDQVSN LVTYLSDEFC  660
LDEKRELSEK VKHAKRLSDE RNLLQDSNFK DINRQPERGW GGSTGITIQG GDDVFKENYV  720
TLSGTFDECY PTYLYQKIDE SKLKAFTRYQ LRGYIEDSQD LEIYSIRYNA KHETVNVPGT  780
GSLWPLSAQS PIGKCGEPNR CAPHLEWNPD LDCSCRDGEK CAHHSHHFSL DIDVGCTDLN  840
EDLGVWVIFK IKTQDGHARL GNLEFLEEKP LVGEALARVK RAEKKWRDKR EKLEWETNIV  900
YKEAKESVDA LFVNSQYDQL QADTNIAMIH AADKRVHSIR EAYLPELSVI PGVNAAIFEE  960
LEGRIFTAFS LYDARNVIKN GDFNNGLSCW NVKGHVDVEE QNNQRSVLVV PEWEAEVSQE  1020
VRVCPGRGYI LRVTAYKEGY GEGCVTIHEI ENNTDELKFS NCVEEEIYPN NTVTCNDYTV  1080
NQEEYGGAYT SRNRGYNEAP SVPADYASVY EEKSYTDGRR ENPCEFNRGY RDYTPLPVGY  1140
VTKELEYFPE TDKVWIEIGE TEGTFIVDSV ELLLMEE                          1177

SEQ ID NO: 13           moltype = AA  length = 1743
FEATURE                 Location/Qualifiers
source                  1..1743
                        mol_type = protein
                        note = synthetic
                        organism = synthetic construct
SEQUENCE: 13
MEVDVRITTA ALLIFAATLV SAQTNQLRCT YIQEIPRGDT PVFNFPSFDG VPWSQQPLLP  60
LPQREELCME DPVSAGSSVI MTIYMEEEIE EEIAIAKLNY KGTGTPEIGP AFTTGSFHTL  120
GPVFRRIPED GEWHLVITNK QDFEAPNMQR YWFDISVPGE SVGLMVLLEI VNIDDNAPIV  180
HMIDRCEIPE PGTHGRTACA YTVSDADGRI STEFMTYKID SDRNDQDFFE LVNDHTMDAD  240
EKITHMVLYL HKDLDFEVNP LHIFSVTAFD SKPNEHEVTM MVQVQNTDRR NPRWLDIFAV  300
QQFNEKQAKS FTVRAIDGDT GINKPIFYRI ETEDEDKEFF SIENMGEGRD GARFHVAPID  360
RDYLKRDMFH IRIIAYKQGD NDKEGESSFE TSANVTIIIN DINDQRPEPF HKEYTISIME  420
ETAMTLDLQE FGFHDRDIGP HAQYDVHLES IQPDGAHTAF YIAPEEGYQA QSFTIGTRIH  480
NMLDYEDDDY RPGIKLKAVA IDRHDNNHIG EAIININLIN WNDELPIFDE DAYNVTFEET  540
VGDGFHVGKY RAKDRDIGDI VEHSILGNAA NFLRIDIETG DVYVSRDDYF DYQRQNEIIV  600
QILAVDTLGL PQNRATTQLT IFLEDINNTP PILRLPRSSP SVEENVEVGH PITEGLTATD  660
PDTTADLHFE IDWDNSYATK QGTNGPNTAD YHGCVEILTV YPDPHNRGRA EGHLVAREVS  720
DGVTIDYEKF EVLYLVVRVI DRNTVIGPDY DEAMLTVTII DMNDNWPIWA DNTLQQTLRV  780
REMADEGVIV GTLLATDLDG PLYNRVRYTM VPIKDTPDDL IAINYVTGQL TVNKGQAIDA  840
DDPPRFYLYY KVTASDKCSL DEFFPVCPPD PTYWNTEGEI AIAITDTNNK IPRAETDMFP  900
SEERIYENAP NGTKITTIIA SDQDRDRPNN ALTYRINYAF NHRLENFFAV DPDTGELFVH  960
FTTSEVLDRD GEEPEHRIIF TIVDNLEGAG DGNQNTISTE VRVILLDIND NKPELPIPDG  1020
EFWTVSEGEV EGKRIPPEIH AHDRDEPFND NSRVGYEIRS IKLINRDIEL PQDPFKIITI  1080
DDLDTWKFVG ELETTMDLRG YWGTYDVEIR AFDHGVPMLD SFETYQLTVR PYNFHSPVFV  1140
FPTPGSTIRL SRERAIVNGM LALANIASGE FLDRLSATDE DGLHAGRVTF SIAGNDEAAE  1200
YFNVLNDGDN SAMLTLKQAL PAGVQQFELV IRATDGGTEP GPRSTDCSVT VVFVMTQGDP  1260
VFDDNAASVR FVEKEAGMSE RFQLPQADDP KNYRCMDDCH TIYYSIVDGN DGDHFAVEPE  1320
TNVIYLLKPL DRSQQEQYRV VVAASNTPGG TSTLSSSLLT VTIGVREANP RPIFESEFYT  1380
AGVLHTDSIH KELVYLAAKH SEGLPIVYSI DQETMKIDES LQTVVEDAFD INSATGVISL  1440
NFQPTSVMHG SFDFEVVASD TRGASDRAKV SIYMISTRVR VAFLFYNTEA EVNERRNFIA  1500
QTFANAFGMT CNIDSVLPAT DANGVIREGY TELQAHFIRD DQPVPADYIE GLFTELNTLR  1560
DIREVLSTQQ LTLLDFAAGG STVLPGGEYA LAVYILAGIA ALLAVICLAL LIAFFIRTRA  1620
LNRRLEALSM TKYGSVDSGL NRAGLAAPGT NKHAIEGSNP IWNETIKAPD FDAISDVSND  1680
SDLIGIEDLP QFRSDYFPPG DDHSLQGIVL DNQNNDTVAT HGNNFKFNAS PFSPEFGNTP  1740
IRR                                                               1743
```

What is claimed is:

1. A modified pesticidal protein for controlling a target pest, wherein the modified pesticidal protein is a modified TIC2160 pesticidal protein or a modified TIC105 pesticidal protein, wherein the modified TIC2160 pesticidal protein is modified by insertion of an amino acid sequence comprising the amino acid sequence of SEQ ID NO:6 in place of residues E747 to K749 of the TIC2160 pesticidal protein to produce the modified TIC2160 pesticidal protein, and wherein the modified TIC105 pesticidal protein is modified by insertion of an amino acid sequence comprising the amino acid sequence of SEQ ID NO:9 in place of residues G342 to A344 of the TIC105 pesticidal protein to produce the modified TIC105 pesticidal protein.

2. The modified pesticidal protein of claim 1, wherein the modified pesticidal protein has enhanced pesticidal activity as compared to the corresponding unmodified TIC2160 or TIC105 pesticidal protein.

3. The modified pesticidal protein of claim 1, wherein the modified pesticidal protein is a modified TIC2160 pesticidal protein that comprises the amino acid sequence of SEQ ID NO:7.

4. The modified pesticidal protein of claim 1, wherein the modified pesticidal protein is a modified TIC105 pesticidal protein that comprises the amino acid sequence of SEQ ID NO:10.

5. The modified pesticidal protein of claim 1, wherein said target pest is selected from the group consisting of a Lepidopteran insect, a Coleopteran insect, a Hemipteran insect, a Homopteran insect, a Hymenopteran insect, a Dipteran insect, a nematode, a pathogenic microorganism, a pathogenic fungi, and a pathogenic bacterium.

6. A plant or plant cell comprising a pesticidally effective amount of the modified pesticidal protein of claim 1.

7. A seed produced from the plant of claim 6, wherein said seed comprises a polynucleotide molecule encoding said modified pesticidal protein in its genome.

8. The plant or plant cell of claim 6, further comprising:

a) a pesticidal agent toxic to said target pest, wherein said pesticidal agent is different from said modified pesticidal protein and is selected from the group consisting of a bacterial toxin, a plant toxin, an arachnid toxin, and a dsRNA targeting for suppression an essential gene in said target pest; or b) a pesticidal agent toxic to a different pest, wherein said pesticidal agent is different from said modified pesticidal protein and is selected from the group consisting of a bacterial toxin, a plant toxin, an arachnid toxin, and a dsRNA targeting for suppression an essential gene in said different pest.

9. A recombinant polynucleotide molecule encoding the modified pesticidal protein of claim 1.

10. A polynucleotide construct comprising the recombinant polynucleotide molecule of claim 9.

11. A composition comprising the modified pesticidal protein of claim 1 for topical application to the target pest or to a crop plant.

12. A plant comprising a plant genome comprising the recombinant polynucleotide molecule of claim 9.

* * * * *